United States Patent [19]
Terman et al.

[11] Patent Number: 5,861,301
[45] Date of Patent: Jan. 19, 1999

[54] RECOMBINANT KINASE INSERT DOMAIN CONTAINING RECEPTOR AND GENE ENCODING SAME

[75] Inventors: Bruce Israel Terman, Monroe; Miguel Eduardo Carrion, Spring Valley, both of N.Y.

[73] Assignee: American Cayanamid Company, Madison, N.J.

[21] Appl. No.: 930,548

[22] PCT Filed: Feb. 20, 1992

[86] PCT No.: PCT/US92/01300

§ 371 Date: Nov. 23, 1992

§ 102(e) Date: Nov. 23, 1992

[87] PCT Pub. No.: WO92/14248

PCT Pub. Date: Sep. 3, 1992

[51] Int. Cl.⁶ .............................. C12N 1/21; C07H 21/04
[52] U.S. Cl. ...................................... 435/252.3; 435/320.1; 536/23.5; 536/24.31; 530/350; 935/9
[58] Field of Search ............................... 536/23.5, 24.31; 435/69.1, 172.1, 172.3, 240.1, 252.3, 320.1, 183; 530/350, 351, 399; 935/9, 19

[56] References Cited

U.S. PATENT DOCUMENTS

| | | | |
|---|---|---|---|
| 4,743,679 | 5/1988 | Cohen et al. | 530/350 |
| 4,966,841 | 10/1990 | Riley | 435/69.1 |
| 5,283,354 | 2/1994 | Lemischka | 536/23.5 |

OTHER PUBLICATIONS

R.G.K. Gronwald et al., PNAS 85:34535–3439, May 1988.
J.U. Bowie etal., Science 247:1306, 16 Mar. 1990.
M. Shibuya et al., Oncogene 5:519–524, 1990.

Primary Examiner—Stephen Walsh
Assistant Examiner—L. Spector
Attorney, Agent, or Firm—Alan M. Gordon; Elizabeth M. Barnhard

[57] ABSTRACT

A DNA sequence encoding a novel human growth factor receptor referred to as a type III receptor tyrosine kinase is described. The amino acid sequence of the receptor is also described. The receptor has a sequence which is similar to that of the kinase domains of known type III receptor tyrosine kinases, but which is unique in its kinase insert domain sequence. The receptor binds specifically to the vascular endothelial cell growth factor.

9 Claims, 28 Drawing Sheets

FIG. 2

PRIMER 1

RECEPTOR

```
PDGF         AAC CTG TTG GGG GCC TGC ACC
ckit           T   A   T   A
CSF            T           
FGF                    C               G
```

PRIMER 1    GTCGAC AAC CTG TTG GGG GCC TGC AAC
                       T             A

PRIMER 2

RECEPTOR

```
PDGF         CAC AGA GAC CTG GCG GCT AGG AAC GTG CT
ckit             T   G   GA  C   A   T       A
CSF          C G         A   GC  C       T    C
FGF          C           C   C       C   T C
```

CONSENSUS    CAC AGA GAC CTG GCC GCT AGI AAC GTG CT
                 C                   T   C       T

PRIMER 2     GAATTC AG CAC GTT ICT AGC CGC CAG GTC TCT GTG
                           T   G   T                     G

```
ATG GAG AGC AAG GTG CTG CTG GCC GTC CTG CTG TGG CTC TGC GTG GAG ACC CGG
Met Glu Ser Lys Val Leu Leu Ala Val Leu Leu Trp Leu Cys Val Glu Thr Arg>

GCC GCC TCT GTG GGT TTG CCT AGT GTT TCT CTT GAT CTG CCC AGG CTC AGC ATA
Ala Ala Ser Val Gly Leu Pro Ser Val Ser Leu Asp Leu Pro Arg Leu Ser Ile>

CAA AAA GAC ATA CTT ACA ATT AAG GCT ACA ACT CTT CAA ATT ACT TGC AGG
Gln Lys Asp Ile Leu Thr Ile Lys Ala Thr Thr Leu Gln Ile Thr Cys Arg>

GGA CAG AGG GAC TTG GAC TGG CTT TGG CCC AAT AAT CAG AGT GGC AGT GAG CAA
Gly Gln Arg Asp Leu Asp Trp Leu Trp Pro Asn Asn Gln Ser Gly Ser Glu Gln>

AGG GTG GAG GTG ACT GAG TGC Cys AGC GAT GGC CTC TTC TGT AAG ACA CTC ACA ATT
Arg Val Glu Val Thr Glu Cys Ser Asp Gly Leu Phe Cys Lys Thr Leu Thr Ile>

CCA AAA GTG ATC GGA AAT GAC ACT GGA GCC TAC AAG TGC Cys TTC TAC CGG GAA ACT
Pro Lys Val Ile Gly Asn Asp Thr Gly Ala Tyr Lys Cys Phe Tyr Arg Glu Thr>
```

FIG. 7A

```
                  330               340               350               360               370
                   *                 *                 *                 *                 *
         GAC TTG GCC TCG GTC ATT TAT GTC TAT GTT CAA GAT TAC AGA TCT CCA TTT ATT
         Asp Leu Ala Ser Val Ile Tyr Val Tyr Val Gln Asp Tyr Arg Ser Pro Phe Ile>

380               390               400               410               420               430
           *                 *                 *                 *                 *                 *
         GCT TCT GTT AGT GAC CAA CAT GGA GTC GTG TAC ATT ACT GAG AAC AAA AAC AAA
         Ala Ser Val Ser Asp Gln His Gly Val Val Tyr Ile Thr Glu Asn Lys Asn Lys>

440               450               460               470               480
                   *                 *                 *                 *                 *
         ACT GTG GTG ATT CCA TGT CTC GGG TCC ATT TCA AAT CTC AAC GTG TCA CTT TGT
         Thr Val Val Ile Pro Cys Leu Gly Ser Ile Ser Asn Leu Asn Val Ser Leu Cys>

490               500               510               520               530               540
           *                 *                 *                 *                 *                 *
         GCA AGA TAC CCA GAA AAG AGA TTT GTT CCT GAT GGT AAC AGA ATT TCC TGG GAC
         Ala Arg Tyr Pro Glu Lys Arg Phe Val Pro Asp Gly Asn Arg Ile Ser Trp Asp>

550               560               570               580               590
                   *                 *                 *                 *                 *
         AGC AAG AAG GGC TTT ACT ATT CCC AGC TAC ATG ATC AGC TAT GCT GGC ATG GTC
         Ser Lys Lys Gly Phe Thr Ile Pro Ser Tyr Met Ile Ser Tyr Ala Gly Met Val>

600               610               620               630               640
           *                 *                 *                 *                 *
         TTC TGT GAA GCA AAA ATT AAT GAT GAA AGT TAC CAG TCT ATT ATG TAC ATA GTT
         Phe Cys Glu Ala Lys Ile Asn Asp Glu Ser Tyr Gln Ser Ile Met Tyr Ile Val>
```

FIG. 7B

```
650
 *
GTC GTT GTA GGG TAT AGG ATT TAT GAT GTG GTT CTG AGT CCG TCT CAT GGA ATT
Val Val Val Gly Tyr Arg Ile Tyr Asp Val Val Leu Ser Pro Ser His Gly Ile>
                     660         670         680         690         700
                      *           *           *           *            *

GAA CTA TCT GTT GGA GAA AAG CTT GTC TTA GTC TTA AAT TGT [Cys] THR ACA GCA AGA ACT GAA CTA
Glu Leu Ser Val Gly Glu Lys Leu Val Leu Val Leu Asn Cys Thr Ala Arg Thr Glu Leu>
     710         720         730         740         750         810
      *           *           *           *           *            *

AAT GTG GGG ATT GAC TTC AAC TGG GAA TAC CCT TCT TCG AAG CAT CAG CAT AAG
Asn Val Gly Ile Asp Phe Asn Trp Glu Tyr Pro Ser Ser Lys His Gln His Lys>
760          770         780         790         800
 *            *           *           *           *

AAA CTT GTA AAC CGA GAC CTA AAA ACC CAG TCT GGG AGT GAG ATG AAG AAA TTT
Lys Leu Val Asn Arg Asp Leu Lys Thr Gln Ser Gly Ser Glu Met Lys Lys Phe>
                     820         830         840         850         860
                      *           *           *           *            *

TTG AGC ACC TTA ACT ATA GAT GGT GTA ACC CGG AGT GAC CAA GGA TTG TAC ACC
Leu Ser Thr Leu Thr Ile Asp Gly Val Thr Arg Ser Asp Gln Gly Leu Tyr Thr>
     870         880         890         900         910
      *           *           *           *           *

TGT GCA GCA TCC AGT GGG CTG ATG ACC AAG AAG AAC AGC ACA TTT GTC AGG GTC
Cys Ala Ala Ser Ser Gly Leu Met Thr Lys Lys Asn Ser Thr Phe Val Arg Val>
920          930         940         950         960         970
 *            *           *              *           *            *

FIG. 7C
```

```
CAT GAA AAA CCT TTT GTT GCT TTT GGA AGT GGC ATG GAA TCT CTG GTG GAA GCC
His Glu Lys Pro Phe Val Ala Phe Gly Ser Gly Met Glu Ser Leu Val Glu Ala>

ACG GTG GGG GAG CGT GTC AGA ATC CCT GCG AAG TAC CTT TAT CTT GGT TAC CCA CCC CCA
Thr Val Gly Glu Arg Val Arg Ile Pro Ala Lys Tyr Leu Gly Tyr Pro Pro Pro>

GAA ATA AAA TGG TAT AAA AAT GGA ATA CCC CTT GAG TCC AAT CAC ACA ATT AAA
Glu Ile Lys Trp Tyr Lys Asn Gly Ile Pro Leu Glu Ser Asn His Thr Ile Lys>

GCG GGG CAT GTA CTG ACG ATT ATG GAA GTG AGT GAA AGA GAC ACA GGA AAT TAC
Ala Gly His Val Leu Thr Ile Met Glu Val Ser Glu Arg Asp Thr Gly Asn Tyr>

ACT GTC ATC CTT ACC AAT CCC ATT TCA AAG GAG AAG CAG AGC CAT GTG GTC TCT
Thr Val Ile Leu Thr Asn Pro Ile Ser Lys Glu Lys Gln Ser His Val Val Ser>

CTG GTT GTG TAT GTC CCA CCC CAG ATT GGT GAG AAA TCT CTA ATC TCT CCT GTG
Leu Val Val Tyr Val Pro Pro Gln Ile Gly Glu Lys Ser Leu Ile Ser Pro Val>
```

FIG. 7D

```
1300
 *
GAT TCC TAC CAG TAC GGC ACC ACT CAA ACG CTG ACA TGT Cys TAT GCC ATT
Asp Ser Tyr Gln Tyr Gly Thr Thr Gln Thr Leu Thr Cys Tyr Ala Ile>
                    1310        1320        1330        1340       1350
                     *           *           *           *          *

1400
                                                             *
CCT CCC CCG CAT CAC ATC CAC TGG TAT TGG CAG TTG GAG GAA GAG TGC GCC AAC
Pro Pro Pro His His Ile His Trp Tyr Trp Gln Leu Glu Glu Glu Cys Ala Asn>
       1360        1370        1380        1390             1400
        *           *           *           *

1410
 *
GAG CCC AGC CAA GCT GTC TCA GTG ACA AAC CCA TAC CCT TGT Cys GAA GAA TGG AGA
Glu Pro Ser Gln Ala Val Ser Val Thr Asn Pro Tyr Pro Cys Glu Glu Trp Arg>
       1420        1430        1440        1450                  1510
        *           *           *           *                     *

1460
 *
AGT GTG GAG GAC TTC CAG GGA AAT GGA AAT ATT GAA GTT AAT AAA AAT CAA TTT
Ser Val Glu Asp Phe Gln Gly Asn Gly Asn Ile Glu Val Asn Lys Asn Gln Phe>
       1470        1480        1490        1500        1510
        *           *           *           *           *

1560
                                                                  *
GCT CTA ATT GAA GGA AAA AAC ACT GTA AGT ACC CTT GTT ATC CAA GCG GCA
Ala Leu Ile Glu Gly Lys Asn Thr Val Ser Thr Leu Val Ile Gln Ala Ala>
       1520        1530        1540        1550        1560
        *           *           *           *

1570                                                              1620
 *                                                                 *
AAT GTG TCA GCT TTG TAC AAA TGT Cys GAA GCG GTC AAC AAA GTC GGG AGA GGA GAG
Asn Val Ser Ala Leu Tyr Lys Cys Glu Ala Val Asn Lys Val Gly Arg Gly Glu>
       1580        1590        1600        1610        1620
        *           *           *           *

FIG. 7E
```

```
                    1630        1640        1650        1660        1670
                      *           *           *           *           *
AGG GTG ATC TCC TTC CAC GTG ACC AGG GGT CCT GAA ATT ACT TTG CAA CCT GAC
Arg Val Ile Ser Phe His Val Thr Arg Gly Pro Glu Ile Thr Leu Gln Pro Asp>

1680        1690        1700        1710        1720
          *           *           *           *           *
ATG CAG CCC ACT GAG CAG GAG AGC GTG TCT TTG TGG TGC ACT GCA GAC AGA TCT
Met Gln Pro Thr Glu Gln Glu Ser Val Ser Leu Trp Cys Thr Ala Asp Arg Ser>

1730        1740        1750        1760        1770        1780
  *           *           *           *           *           *
ACG TTT GAG AAC CTC ACA TGG TAC AAG CTT TAC AAG CTT GGC CCA CAG CCT CTG CCA ATC CAT
Thr Phe Glu Asn Leu Thr Trp Tyr Lys Leu Tyr Lys Leu Gly Pro Gln Pro Leu Pro Ile His>

1790        1800        1810        1820        1830
          *           *           *           *           *
GTG GGA GAG TTG CCC ACA CCT GTT TGC AAG AAC TTG GAT ACT CTT TGG AAA TTG
Val Gly Glu Leu Pro Thr Pro Val Cys Lys Asn Leu Asp Thr Leu Trp Lys Leu>

1840        1850        1860        1870        1880        1890
  *           *           *           *           *           *
AAT GCC ACC ATG TTC TCT AAT AGC ACA AAT GAC ATT ATG GAG CTT AAG
Asn Ala Thr Met Phe Ser Asn Ser Thr Asn Asp Ile Met Glu Leu Lys>

1900        1910        1920        1930        1940
          *           *           *           *           *
AAT GCA TCC TTG CAG GAC CAA GGA GAC TAT GTC TGC CTT GCT CAA GAC AGG AAG
Asn Ala Ser Leu Gln Asp Gln Gly Asp Tyr Val Cys Leu Ala Gln Asp Arg Lys>

FIG. 7F
```

```
        1950                1960                1970                1980                1990
           *                   *                   *                   *                   *
ACC AAG AAA AGA CAT TGC GTG GTC AGG CAG CTC ACA GTC CTA GAG CGT GTG GCA
Thr Lys Lys Arg His [Cys] Val Val Arg Gln Leu Thr Val Leu Glu Arg Val Ala>

2000                2010                2020                2030                2040                2050
   *                   *                   *     *             *                   *                   *
CCC ACG ATC ACA GGA AAC CTG GAG AAT CAG ACG ACA AGT ATT GGG GAA AGC ATC
Pro Thr Ile Thr Gly Asn Leu Glu Asn Gln Thr Thr Ser Ile Gly Glu Ser Ile>

2060                2070                2080                2090                2100
               *                   *                   *                   *                   *
GAA GTC TCA TGC ACG GCA TCT GGG AAT CCC CCT CCA CAG ATC ATG TGG TTT AAA
Glu Val Ser [Cys] Thr Ala Ser Gly Asn Pro Pro Pro Gln Ile Met Trp Phe Lys>

2110                2120                2130                2140                2150                2160
       **                  *                   *                   *                   *                   *
GAT AAT GAG ACC CTT GTA GAA GAC TCA GGC ATT GTA TTG AAG GAT GGG AAC CGG
Asp Asn Glu Thr Leu Val Glu Asp Ser Gly Ile Val Leu Lys Asp Gly Asn Arg>

2170                2180                2190                2200                2210
*                  *                   *                   *                   *                   *
AAC CTC ACT ATC CGC AGA GTG AGG AAG GAG GAC GAA GGC CTC TAC ACC TGC CAG
Asn Leu Thr Ile Arg Arg Val Arg Lys Glu Asp Glu Gly Leu Tyr Thr [Cys] Gln>

2220                2230                2240                2250                2260
           *                   *                   *                   *                   *
GCA TGC AGT GTT CTT GGC TGT GCA AAA GTG GAG GCA TTT TTC ATA ATA GAA GGT
Ala [Cys] Ser Val Leu Gly [Cys] Ala Lys Val Glu Ala Phe Phe Ile Ile Glu Gly>
```

FIG. 7G

```
2270
  *
GCC CAG GAA AAG ACG AAC TTG GAA ATC ATT ATT CTA GTA GGC ACG GTG ATT
Ala Gln Glu Lys Thr Asn Leu Glu Ile Ile Ile Leu Val Gly Thr Val Ile>
              2280        2290        2300        2310        2320
                *           *           *           *           *

2330        2340        2350        2360        2370
              *           *           *           *           *
GCC ATG TTC TTC TGG CTA CTT CTT GTC ATC ATC CTA GGG ACC GTT AAG CGG GCC
Ala Met Phe Phe Trp Leu Leu Leu Val Ile Ile Leu Gly Thr Val Lys Arg Ala>

2380        2390        2400        2410        2420        2430
              *           *           *           *           *           *
AAT GGA GGG GAA CTG AAG ACA GGC TAC TTG TCC ATC GTC ATG GAT CCA GAT GAA
Asn Gly Gly Glu Leu Lys Thr Gly Tyr Leu Ser Ile Val Met Asp Pro Asp Glu>

2440        2450        2460        2470        2480
              *           *           *           *           *
CTC CCA TTG GAT GAA CAT TGT GAA CGA CTG CCT TAT GAT GCC AGC AAA TGG GAA
Leu Pro Leu Asp Glu His Cys Glu Arg Leu Pro Tyr Asp Ala Ser Lys Trp Glu>

2490        2500        2510        2520        2530
              *           *           *           *           *
TTC CCC AGA GAC CGG CTG AAC CTA GGT AAG CCT CTT GGC CGT GGT GCC TTT GGC
Phe Pro Arg Asp Arg Leu Asn Leu Gly Lys Pro Leu Gly Arg Gly Ala Phe Gly>

2540        2550        2560        2570        2580        2590
  *           *           *           *           *           *
CAA GAG ATT GAA GCA GAT GCC TTT GGA ATT GAC AAG ACA GCA ACT TGC AGG ACA
Gln Glu Ile Glu Ala Asp Ala Phe Gly Ile Asp Lys Thr Ala Thr Cys Arg Thr>
```

FIG. 7H

```
            2600                2610                 2620                 2630                 2640
              *                   *                    *                    *                    *
GTA GCA GTC AAA ATG TTG AAA GAA GGA GCA ACA CAC AGT GAG CAT CGA GCT CTC
Val Ala Val Lys Met Leu Lys Glu Gly Ala Thr His Ser Glu His Arg Ala Leu>

2650                2660                 2670                 2680                 2690                 2700
       *                   *                    *                    *                    *                    *
ATG TCT GAA CTC AAG ATC CTC ATT CAT ATT GGT CAC CAT CTC AAT GTG GTC AAC
Met Ser Glu Leu Lys Ile Leu Ile His Ile Gly His His Leu Asn Val Val Asn>

2710                 2720                 2730                 2740                 2750
              *                    *                    *                    *                    *
CTT CTA GGT GCC TGT ACC AAG CCA GGA GGG CCA CTC ATG GTG ATT GTG GAA TTC
Leu Leu Gly Ala Cys Thr Lys Pro Gly Gly Pro Leu Met Val Ile Val Glu Phe>

2760                2770                 2780                 2790                 2800
       *                   *                    *                    *                    *
TGC AAA TTT GGA AAC CTG TCC ACT TAC CTG AGG AGC AAG AGA AAT GAA TTT GTC
Cys Lys Phe Gly Asn Leu Ser Thr Tyr Leu Arg Ser Lys Arg Asn Glu Phe Val>

2810                 2820                 2830                 2840                 2850                 2860
              *                    *                    *                    *                    *                    *
CCC TAC AAG ACC AAA GGG GCA CGA TTC CGT CAA GGG AAA GAC TAC GTT GGA GCA
Pro Tyr Lys Thr Lys Gly Ala Arg Phe Arg Gln Gly Lys Asp Tyr Val Gly Ala>

2870                2880                 2890                 2900                 2910
       *                   *                    *                    *                    *
ATC CCT GTG GAT CTG AAA CGG CGC TTG GAC AGC ATC ACC AGT AGC CAG AGC TCA
Ile Pro Val Asp Leu Lys Arg Arg Leu Asp Ser Ile Thr Ser Ser Gln Ser Ser>
```

FIG. 7I

```
            2920      2930      2940      2950      2960      2970
              *         *         *         *         *         *
            GCC AGC TCT GGA TTT GTG GAG GAG AAG TCC CTC AGT GAT GTA GAA GAG GAA
            Ala Ser Ser Gly Phe Val Glu Glu Lys Ser Leu Ser Asp Val Glu Glu Glu>

2980      2990      3000      3010      3020
                        *         *         *         *         *
            GCT CCT GAA GAT CTG TAT AAG GAC TTC CTG ACC TTG GAG CAT CTC ATC TGT TAC
            Ala Pro Glu Asp Leu Tyr Lys Asp Phe Leu Thr Leu Glu His Leu Ile Cys Tyr>

3030      3040      3050      3060      3070
              *         *         *         *         *
            AGC TTC CAA GTG GCT AAG GGC ATG GAG TTC TTG GCA TCG CGA AAG TGT ATC CAC
            Ser Phe Gln Val Ala Lys Gly Met Glu Phe Leu Ala Ser Arg Lys Cys Ile His>

3080      3090      3100      3110      3120      3130
              *         *         *         *         *         *
            AGG GAC CTG GCG GCA CGA AAT ATC CTC TTA TCG GAG AAG AAC GTG GTT AAA ATC
            Arg Asp Leu Ala Ala Arg Asn Ile Leu Leu Ser Glu Lys Asn Val Val Lys Ile>

3140      3150      3160      3170      3180
                        *         *         *         *         *
            TGT GAC TTT GGC TTG GCC CGG GAT ATT TAT AAA GAT CCA GAT TAT GTC AGA AAA
            Cys Asp Phe Gly Leu Ala Arg Asp Ile Tyr Lys Asp Pro Asp Tyr Val Arg Lys>

3190      3200      3210      3220      3230      3240
              *         *         *         *         *         *
            GGA GAT GCT CGC CTC CCT TTG AAA TGG ATG GCC CCA GAA ACA ATT TTT GAC AGA
            Gly Asp Ala Arg Leu Pro Leu Lys Trp Met Ala Pro Glu Thr Ile Phe Asp Arg>
```

FIG. 7J

```
                    3250                    3260                    3270                    3280                    3290
                      *                       *                       *                       *                       *
            GTG TAC ACA ATC CAG AGT GAC GTC TGG TCT TTT GGT GTT TTG CTG TGG GAA ATA
            Val Tyr Thr Ile Gln Ser Asp Val Trp Ser Phe Gly Val Leu Leu Trp Glu Ile>

3300                    3310                    3320                    3330                    3340                    3400
      *                       *                       *                       *                       *                       *
    TTT TCC TTA GGT GCT TCT CCA TAT CCT GGG GTA AAG ATT GAT GAA GAA TTT TGT
    Phe Ser Leu Gly Ala Ser Pro Tyr Pro Gly Val Lys Ile Asp Glu Glu Phe Cys>

3350                    3360                    3370                    3380                    3390
  *                       *                       *                       *                       *
AGG CGA TTG AAA GAA GGA ACT AGA ATG AGG GCC CCT GAT TAT ACT ACA CCA GAA
Arg Arg Leu Lys Glu Gly Thr Arg Met Arg Ala Pro Asp Tyr Thr Thr Pro Glu>

3410                    3420                    3430                    3440                    3450
          *                       *                       *                       *                       *
        ATG TAC CAG ACC ATG CTG GAC TGC TGG CAC GGG GAG CCC AGT CAG AGA CCC ACG
        Met Tyr Gln Thr Met Leu Asp Cys Trp His Gly Glu Pro Ser Gln Arg Pro Thr>

3460                    3470                    3480                    3490                    3500                    3510
      *                       *                       *                       *                       *                       *
    TTT TCA GAG TTG GTG GAA CAT TTG GGA AAT CTC TTG CAA GCT AAT GCT CAG CAG
    Phe Ser Glu Leu Val Glu His Leu Gly Asn Leu Leu Gln Ala Asn Ala Gln Gln>

3520                    3530                    3540                    3550                    3560
                  *                       *                       *                       *                       *
                GAT GGC AAA GAC TAC ATT GTT CTT CCG ATA TCA GAG ACT TTG AGC ATG GAA GAG
                Asp Gly Lys Asp Tyr Ile Val Leu Pro Ile Ser Glu Thr Leu Ser Met Glu Glu>
```

FIG. 7K

```
3570
  *
GAT TCT GGA CTC TCT CTG CCT ACC TCA CCT GTT TCC TGT ATG GAG GAG GAG GAA
Asp Ser Gly Leu Ser Leu Pro Thr Ser Pro Val Ser Cys Met Glu Glu Glu Glu>
        3580        3590        3600        3610
          *           *           *           *

3620        3630        3640        3650        3660        3670
  *           *           *           *           *           *
GTA TGT GAC CCC AAA TTC CAT TAT GAC AAC ACA GCA GGA ATC AGT CAG TAT CTG
Val Cys Asp Pro Lys Phe His Tyr Asp Asn Thr Ala Gly Ile Ser Gln Tyr Leu>

3680        3690        3700        3710        3720
          *           *           *           *           *
CAG AAC AGT AAG CGA AAG AGC CGG CCT GTG AGT GTA AAA ACA TTT GAA GAT ATC
Gln Asn Ser Lys Arg Lys Ser Arg Pro Val Ser Val Lys Thr Phe Glu Asp Ile>

3730        3740        3750        3760        3770        3780
  *           *           *           *           *           *
CCG TTA GAA GAA CCA GAA GTA AAA GTA ATC CCA GAT GAC AAC CAG ACG GAC AGT
Pro Leu Glu Glu Pro Glu Val Lys Val Ile Pro Asp Asp Asn Gln Thr Asp Ser>

3790        3800        3810        3820        3830
          *           *           *           *           *
GGT ATG GTT CTT GCC TCA GAA GAG CTG AAA ACT TTG GAA GAC AGA ACC AAA TTA
Gly Met Val Leu Ala Ser Glu Glu Leu Lys Thr Leu Glu Asp Arg Thr Lys Leu>

3840        3850        3860        3870        3880
  *           *           *           *           *
TCT CCA TCT TTT GGT GGA ATG GTG CCC AGC AAA AGC AGG GAG TCT GTG GCA TCT
Ser Pro Ser Phe Gly Gly Met Val Pro Ser Lys Ser Arg Glu Ser Val Ala Ser>
```

FIG. 7L

```
3890        3900           3910           3920           3930           3940
 *           *              *              *              *              *
       GAA GGC TCA AAC CAG ACA AGC GGC TAC CAG TCC GGA TAT CAC TCC GAT GAC ACA
       Glu Gly Ser Asn Gln Thr Ser Gly Tyr Gln Ser Gly Tyr His Ser Asp Asp Thr>

3950           3960           3970           3980           3990
        *              *              *              *              *
       GAC ACC ACC GTG TAC TCC AGT GAG GAA GCA GAA CTT TTA AAG CTG ATA GAG ATT
       Asp Thr Thr Val Tyr Ser Ser Glu Glu Ala Glu Leu Leu Lys Leu Ile Glu Ile>

4000           4010           4020           4030           4040           4050
 *              *              *              *              *              *
GGA GTG CAA ACC GGT AGC ACA GCC CAG ATT CTC CAG CCT GAC ACG GGG ACC ACA
Gly Val Gln Thr Gly Ser Thr Ala Gln Ile Leu Gln Pro Asp Thr Gly Thr Thr>

4060           4070
        *              *
       CTG AGC TCT CCT CCT GTT TAA
       Leu Ser Ser Pro Pro Val ***
```

FIG. 7M

```
KDR   787  GTVKRANGGELKTGYLSIVMDPDELPLDEHCERLPYDASKWEFPRDRLNLGK
ckit  543  L*YLQKPMYEVQWKVVEEINGNNYVYIDPTQH-*NSF**
CSF1  536  LLY*YKQKPKYQVRWKIIESYEGNSYTFIDPTQ***NE-******NN*QF**
PDGF  522  MLWQKKPRYEIRWKVIESVSSDGHEYIYVDPVQ****-ST*****QLV**R
                   *   * *
KDR   839  PLGRGAFGQEIEADAFGIDKTATCRTVAVKMLKEGATHSEHRALMSELKILI
ckit  594  TA**KVVAET*Y*LI*SDAAM********PS*HLT*RE*****V*S
CSF1  587  TAKVVT***LG*EDAVLK*******ST*HAD*KE******MS
PDGF  573  TS*VVT**H*LSHSQATMK******ST*RSS*KQS*****MS KDR   891  HIGHHLNVVNLLGACTKPGGPLMVIVEFCKFGNLSTYLRSKRNEFVPYKTKG
ckit  646  YL**N*M*I******I-*TL**T*Y*CY*D*LNFRDS*ICS*QED
CSF1  639  *L*Q*E*I********H-****VL**T*Y*CY*D*LNF**R*AEAMLGPSLSP
PDGF  625  *L*P********-**IYI*T*Y*RY*D*VD**HRNKHT*LQRHSNK KDR   943  ARFRQGKDYVGAIPVDLKRRLDSIT-SSQSSASSGFVEEKSL------SDV
ckit  697  HAEA-A-L*KNLLHSKESSCS-DS*N-E----YMDMKPGVS--YVVPT--KA
CSF1  690  GQDPE*GVDYKN*HLEK*YVRRDSGF***GVDTYVEMRPVSTSS-NDSF*EQ
PDGF  676  HCPPSAEL*SN*LP*GFSLPSHLNLTGESDGGYMDMSKDESIDYVPMLDMKG KDR   987  EEEEAPEDLYKDF-------------LTLEHLICYSFQV
ckit  737  D-KRRSVRIGSYI--------ERDVTPAIMEDDELA*D**D*LSF*Y**
CSF1  741  DLDKEDGRPL-----------------E*RD*LHF*S**
PDGF  728  DIKY*DIESPSYMAPYDNYVPSAPERTYRATLINDSPV-*SYTD*VGF*Y**

KDR   1013 AKGMEFLASRKCIHRDLAARNILLSEKNVVKICDFGLARDIYKDPDYVRKGD
```

FIG. 9A

```
ckit    777  -**A**N***********THGRIT****************KN*SNVN
CSF1    762  *Q**A**N***********V*TNGHVAG*********MN*SN*IV**N
PDGF    779  *N*D***N*************V*ICEGKL***************MR*SN*IS**S KDR    1065  ARLPLKWMAPETIFDRVYTIQSDVWSFGVLLWEIFSLGASPYPGVKIDEEFC
ckit    828  **V**SNC**EE**Y*IF********S**MPVKSK*Y
CSF1    814  ****V******S****C***VQ****Y*I***********LN***ILVNSK*Y
PDGF    831  *********S*NS**TL***I*I**********GT*ELPMNDQ*Y KDR    1117  RRLKEGTRMRRAPDYTTPEMYQTMLDCWHGEPSQRPTFSELVEHLGNLLQANA
ckit    880  KMI**FLS*EHAPA***DI*KT**DAD*LK****KQIVQLIEKQISEST
CSF1    862  KLV*D*YQ*AQ*AFAPKNI*SI*QA**AL*.*TH****QQICSF*QEQAQEDR
PDGF    883  NAI*R*Y**AQ*AHASD*I*EI*QKEEKFET*Q**LL*ER**GEGY KDR    1169  QQDGKDYIVLPISETLSMEEDSGLSLPTSPVSCMEEEVCDPKFHYDNTAGI
ckit    932  NHIYSNLANCSPNRQKPVVDHSVRINSVGSTASSSQPLLVHDDV
CSF1    914  RERDYTNLPSSSRSGG*GSSS*E*EEESSSEHLTCC*QGDIAQPLLQPNNYQ
PDGF    934  KKKYQQVDEEFLRSDHPAILR*QARF*GIHSLRSPLDTSSVLYTAVQPNESD KDR    1213  SQYLQNSKRKSRPVSVKTFEDIPLEEPEVKVIPDDNQTDSGMVLASEELKTL
CSF1    966  FC
PDGF    987  ND*IIPLPDPKPD*ADEGLPEGSPSLASSTLNEVNTSSTISCDSPL*LQEEP KDR    1273  EDRTKLSPSFGGMVPSKSRESVASEGSNQTSGYQSGYHSDDTDTTVYSSEEA
PDGF   1039  QQAEPEAQLEQPQDSGCPGPLAEA*DSFLEQPQD**CPGPLAEAEDSFL

KDR    1325  ELLKLIEIGVQTGSTAQILQPDTGTTLSSPPV
```

FIG. 9B

IDENTIFICATION OF kdp mRNA

IDENTIFICATION OF kdp GENE BY SOUTHERN ANALYSIS

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

GTCGACAAYC TGTTGGGRGC CTGCAAC                                                    27

( 2 ) INFORMATION FOR SEQ ID NO:2:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

GAATTCAGCA CKTTNCTRGC YGCCAGGTCT GYGTC                                           35

( 2 ) INFORMATION FOR SEQ ID NO:3:

( i ) SEQUENCE CHARACTERISTICS:
    ( A ) LENGTH: 363 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

GAATTCTGCA AATTTGGAAA CCTGTCCACT TACCTGAGGA CGAAGAGAAA TGAATTTGTC      60

CCCTACAAGA CCAAAGGGGC ACGATTCCGT CAAGGGAAAG ACTACGTTGG AGCAATCCCT     120

GTGGATCTGA AACGGCGCTT GGACACGCAT CACCAGTAGC CAGAGCTCAG CCAGCTCTGG     180

ATTTGTGGAG GAGAAGTCCC TCAGTGATGT AGAAGAAGAG GAAGCTCCTG AAGATCTGTA     240

TAAGGACTTC CTGACCTTGG AGCATCTCAT CTGTTACAGT TTCCAAGTGG CTAAGGGCAT     300

```
GGAGTTCTTG GCATCGCGAA AGTGTATCCA CAGAGACCTG GCAGCCAGGA ACGTGCTGAA      360

TTC                                                                    363
```

( 2 ) INFORMATION FOR SEQ ID NO:4:

( i ) SEQUENCE CHARACTERISTICS:
        ( A ) LENGTH: 251 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GTCGACAATC TGTTGGGGGC CTGCACCATC CCAACATCCT GCTGCTCTAC AACTATTTTT       60

ATGACCGGAG GAGGATCTAC TTGATTCTAG AGTATGCCCC CCGCGGAGCT CTACAAGGAG      120

CTGCAGAAGA GCTGCACATT TGACGAGCAG CGAACAGCCA CGATCATGGA GGAGTTGGCA      180

GATGCTCTAA TGTACTGCCG TGGGAAGAAG GTGATTCACA GAGACCTGGC AGCCAGCAAC      240

GTGCTGAATT C                                                           251
```

( 2 ) INFORMATION FOR SEQ ID NO:5:

( i ) SEQUENCE CHARACTERISTICS:
        ( A ) LENGTH: 510 base pairs
        ( B ) TYPE: nucleic acid
        ( C ) STRANDEDNESS: single
        ( D ) TOPOLOGY: linear ( i i ) MOLECULE TYPE: DNA (genomic)

( x ) PUBLICATION INFORMATION:
        ( A ) AUTHORS: Gronwald, R., et al.
        ( C ) JOURNAL: Proc. Natl. Acad. Sci. U.S.A.
        ( D ) VOLUME: 85
        ( F ) PAGES: 3435-3439
        ( G ) DATE: 1988

( x i ) SEQUENCE DESCRIPTION: SEQ ID NO:5:

```
AACCTGTGGG GGCCTGCACC AAAGGAGGAC CATCTATATC ATCTATATCA TCACTGAGTA       60

CTGCCGCTAC GGAGACCTGG TGGACTACCT GCACCGCAAC AAACACACCT TCCTGCAGCA      120

CCACTCCGAC AAGCGCCGCC CGCCCAGCGC GGAGCTCTAC AGCAATGCTC TGCCCGTTGG      180

GCTCCCCCTG CCCAGCCATG TGTCCTTGAC CGGGGGAGAG CGACGGTGGC TACATGGACA      240

TGAGCAAGGA CGAGTCGGTG GACTATGTGC CCATGCTGGA CATGAAAGGA GACGTCAAAT      300

AGCAGACATC GAGTCCTCCA ACTACATGGC CCCTTACGAT AACTACGTTC CCTCTGCCCC      360

TGAGAGGACC TGCCGAGCAA CTTTGATCAA CGAGTCTCCA GTGCTAAGCT ACATGGACCT      420

CGTGGGCTTC AGCTACCAGG TGGCCAATGG CATGGAGTTC TGGCCTCCAA GAACTGCGTC      480

CACAGAGACC TGGCGGCTAG GAACGTCCTT                                       510
```

( 2 ) INFORMATION FOR SEQ ID NO:6:

( i ) SEQUENCE CHARACTERISTICS:
        ( A ) LENGTH: 255 base pairs
        ( B ) TYPE: nucleic acid
        ( C ) STRANDEDNESS: single
        ( D ) TOPOLOGY: linear ( i i ) MOLECULE TYPE: DNA (genomic)

( x ) PUBLICATION INFORMATION:
        ( A ) AUTHORS: Ruta, M., et al.
        ( C ) JOURNAL: Oncogene
        ( D ) VOLUME: 3

(F) PAGES: 9-15
(G) DATE: 1988

(xi) SEQUENCE DESCRIPTION: SEQ ID NO:6:

```
AACCTGCTGG GGGCCTGCAC GCAGGATGGT CCCTTGTATG TCATCGTGGA GTATGCCTCC      60
AAGGGCAACC TGCGGGAGTA CCTGCAGACC CGGAGGCCCC CAGGGCTGGA ATACTGCTAT     120
AACCCCAGCC ACAACCCAGA GGAGCAGCTC TCCTCCAAGG ACCTGGTGTC CTGCGCCTAC     180
CAGGAGGCCC GAGGCATGGA GTATCTGGCC TCCAAGAAGT GCATACACCG AGACCTGGCA     240
GCCAGGAATG TCCTG                                                      255
```

(2) INFORMATION FOR SEQ ID NO:7:

(i) SEQUENCE CHARACTERISTICS:
    (A) LENGTH: 4236 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..4068

(xi) SEQUENCE DESCRIPTION: SEQ ID NO:7:

```
ATG GAG AGC AAG GTG CTG CTG GCC GTC GCC CTG TGG CTC TGC GTG GAG       48
Met Glu Ser Lys Val Leu Leu Ala Val Ala Leu Trp Leu Cys Val Glu
 1               5                  10                  15

ACC CGG GCC GCC TCT GTG GGT TTG CCT AGT GTT TCT CTT GAT CTG CCC       96
Thr Arg Ala Ala Ser Val Gly Leu Pro Ser Val Ser Leu Asp Leu Pro
                20                  25                  30

AGG CTC AGC ATA CAA AAA GAC ATA CTT ACA ATT AAG GCT AAT ACA ACT      144
Arg Leu Ser Ile Gln Lys Asp Ile Leu Thr Ile Lys Ala Asn Thr Thr
        35                  40                  45

CTT CAA ATT ACT TGC AGG GGA CAG AGG GAC TTG GAC TGG CTT TGG CCC      192
Leu Gln Ile Thr Cys Arg Gly Gln Arg Asp Leu Asp Trp Leu Trp Pro
    50                  55                  60

AAT AAT CAG AGT GGC AGT GAG CAA AGG GTG GAG GTG ACT GAG TGC AGC      240
Asn Asn Gln Ser Gly Ser Glu Gln Arg Val Glu Val Thr Glu Cys Ser
65                  70                  75                  80

GAT GGC CTC TTC TGT AAG ACA CTC ACA ATT CCA AAA GTG ATC GGA AAT      288
Asp Gly Leu Phe Cys Lys Thr Leu Thr Ile Pro Lys Val Ile Gly Asn
                85                  90                  95

GAC ACT GGA GCC TAC AAG TGC TTC TAC CGG GAA ACT GAC TTG GCC TCG      336
Asp Thr Gly Ala Tyr Lys Cys Phe Tyr Arg Glu Thr Asp Leu Ala Ser
                100                 105                 110

GTC ATT TAT GTC TAT GTT CAA GAT TAC AGA TCT CCA TTT ATT GCT TCT      384
Val Ile Tyr Val Tyr Val Gln Asp Tyr Arg Ser Pro Phe Ile Ala Ser
        115                 120                 125

GTT AGT GAC CAA CAT GGA GTC GTG TAC ATT ACT GAG AAC AAA AAC AAA      432
Val Ser Asp Gln His Gly Val Val Tyr Ile Thr Glu Asn Lys Asn Lys
    130                 135                 140

ACT GTG GTG ATT CCA TGT CTC GGG TCC ATT TCA AAT CTC AAC GTG TCA      480
Thr Val Val Ile Pro Cys Leu Gly Ser Ile Ser Asn Leu Asn Val Ser
145                 150                 155                 160

CTT TGT GCA AGA TAC CCA GAA AAG AGA TTT GTT CCT GAT GGT AAC AGA      528
Leu Cys Ala Arg Tyr Pro Glu Lys Arg Phe Val Pro Asp Gly Asn Arg
                165                 170                 175

ATT TCC TGG GAC AGC AAG AAG GGC TTT ACT ATT CCC AGC TAC ATG ATC      576
Ile Ser Trp Asp Ser Lys Lys Gly Phe Thr Ile Pro Ser Tyr Met Ile
                180                 185                 190
```

| | | | | | | | | | | | | | | | | |
|---|---|---|---|---|---|---|---|---|---|---|---|---|---|---|---|---|
| AGC | TAT | GCT | GGC | ATG | GTC | TTC | TGT | GAA | GCA | AAA | ATT | AAT | GAT | GAA | AGT | 624 |
| Ser | Tyr | Ala | Gly | Met | Val | Phe | Cys | Glu | Ala | Lys | Ile | Asn | Asp | Glu | Ser | |
| | | 195 | | | | | 200 | | | | | 205 | | | | |
| TAC | CAG | TCT | ATT | ATG | TAC | ATA | GTT | GTC | GTT | GTA | GGG | TAT | AGG | ATT | TAT | 672 |
| Tyr | Gln | Ser | Ile | Met | Tyr | Ile | Val | Val | Val | Val | Gly | Tyr | Arg | Ile | Tyr | |
| 210 | | | | | 215 | | | | | 220 | | | | | | |
| GAT | GTG | GTT | CTG | AGT | CCG | TCT | CAT | GGA | ATT | GAA | CTA | TCT | GTT | GGA | GAA | 720 |
| Asp | Val | Val | Leu | Ser | Pro | Ser | His | Gly | Ile | Glu | Leu | Ser | Val | Gly | Glu | |
| 225 | | | | | 230 | | | | | 235 | | | | | 240 | |
| AAG | CTT | GTC | TTA | AAT | TGT | ACA | GCA | AGA | ACT | GAA | CTA | AAT | GTG | GGG | ATT | 768 |
| Lys | Leu | Val | Leu | Asn | Cys | Thr | Ala | Arg | Thr | Glu | Leu | Asn | Val | Gly | Ile | |
| | | | | 245 | | | | | 250 | | | | | 255 | | |
| GAC | TTC | AAC | TGG | GAA | TAC | CCT | TCT | TCG | AAG | CAT | CAG | CAT | AAG | AAA | CTT | 816 |
| Asp | Phe | Asn | Trp | Glu | Tyr | Pro | Ser | Ser | Lys | His | Gln | His | Lys | Lys | Leu | |
| | | | 260 | | | | | 265 | | | | | 270 | | | |
| GTA | AAC | CGA | GAC | CTA | AAA | ACC | CAG | TCT | GGG | AGT | GAG | ATG | AAG | AAA | TTT | 864 |
| Val | Asn | Arg | Asp | Leu | Lys | Thr | Gln | Ser | Gly | Ser | Glu | Met | Lys | Lys | Phe | |
| | | 275 | | | | | 280 | | | | | 285 | | | | |
| TTG | AGC | ACC | TTA | ACT | ATA | GAT | GGT | GTA | ACC | CGG | AGT | GAC | CAA | GGA | TTG | 912 |
| Leu | Ser | Thr | Leu | Thr | Ile | Asp | Gly | Val | Thr | Arg | Ser | Asp | Gln | Gly | Leu | |
| | 290 | | | | | 295 | | | | | 300 | | | | | |
| TAC | ACC | TGT | GCA | GCA | TCC | AGT | GGG | CTG | ATG | ACC | AAG | AAG | AAC | AGC | ACA | 960 |
| Tyr | Thr | Cys | Ala | Ala | Ser | Ser | Gly | Leu | Met | Thr | Lys | Lys | Asn | Ser | Thr | |
| 305 | | | | | 310 | | | | | 315 | | | | | 320 | |
| TTT | GTC | AGG | GTC | CAT | GAA | AAA | CCT | TTT | GTT | GCT | TTT | GGA | AGT | GGC | ATG | 1008 |
| Phe | Val | Arg | Val | His | Glu | Lys | Pro | Phe | Val | Ala | Phe | Gly | Ser | Gly | Met | |
| | | | | 325 | | | | | 330 | | | | | 335 | | |
| GAA | TCT | CTG | GTG | GAA | GCC | ACG | GTG | GGG | GAG | CGT | GTC | AGA | ATC | CCT | GCG | 1056 |
| Glu | Ser | Leu | Val | Glu | Ala | Thr | Val | Gly | Glu | Arg | Val | Arg | Ile | Pro | Ala | |
| | | | 340 | | | | | 345 | | | | | 350 | | | |
| AAG | TAC | CTT | GGT | TAC | CCA | CCC | CCA | GAA | ATA | AAA | TGG | TAT | AAA | AAT | GGA | 1104 |
| Lys | Tyr | Leu | Gly | Tyr | Pro | Pro | Pro | Glu | Ile | Lys | Trp | Tyr | Lys | Asn | Gly | |
| | | 355 | | | | | 360 | | | | | 365 | | | | |
| ATA | CCC | CTT | GAG | TCC | AAT | CAC | ACA | ATT | AAA | GCG | GGG | CAT | GTA | CTG | ACG | 1152 |
| Ile | Pro | Leu | Glu | Ser | Asn | His | Thr | Ile | Lys | Ala | Gly | His | Val | Leu | Thr | |
| | 370 | | | | | 375 | | | | | 380 | | | | | |
| ATT | ATG | GAA | GTG | AGT | GAA | AGA | GAC | ACA | GGA | AAT | TAC | ACT | GTC | ATC | CTT | 1200 |
| Ile | Met | Glu | Val | Ser | Glu | Arg | Asp | Thr | Gly | Asn | Tyr | Thr | Val | Ile | Leu | |
| 385 | | | | | 390 | | | | | 395 | | | | | 400 | |
| ACC | AAT | CCC | ATT | TCA | AAG | GAG | AAG | CAG | AGC | CAT | GTG | GTC | TCT | CTG | GTT | 1248 |
| Thr | Asn | Pro | Ile | Ser | Lys | Glu | Lys | Gln | Ser | His | Val | Val | Ser | Leu | Val | |
| | | | | 405 | | | | | 410 | | | | | 415 | | |
| GTG | TAT | GTC | CCA | CCC | CAG | ATT | GGT | GAG | AAA | TCT | CTA | ATC | TCT | CCT | GTG | 1296 |
| Val | Tyr | Val | Pro | Pro | Gln | Ile | Gly | Glu | Lys | Ser | Leu | Ile | Ser | Pro | Val | |
| | | | 420 | | | | | 425 | | | | | 430 | | | |
| GAT | TCC | TAC | CAG | TAC | GGC | ACC | ACT | CAA | ACG | CTG | ACA | TGT | ACG | GTC | TAT | 1344 |
| Asp | Ser | Tyr | Gln | Tyr | Gly | Thr | Thr | Gln | Thr | Leu | Thr | Cys | Thr | Val | Tyr | |
| | | 435 | | | | | 440 | | | | | 445 | | | | |
| GCC | ATT | CCT | CCC | CCG | CAT | CAC | ATC | CAC | TGG | TAT | TGG | CAG | TTG | GAG | GAA | 1392 |
| Ala | Ile | Pro | Pro | Pro | His | His | Ile | His | Trp | Tyr | Trp | Gln | Leu | Glu | Glu | |
| | 450 | | | | | 455 | | | | | 460 | | | | | |
| GAG | TGC | GCC | AAC | GAG | CCC | AGC | CAA | GCT | GTC | TCA | GTG | ACA | AAC | CCA | TAC | 1440 |
| Glu | Cys | Ala | Asn | Glu | Pro | Ser | Gln | Ala | Val | Ser | Val | Thr | Asn | Pro | Tyr | |
| 465 | | | | | 470 | | | | | 475 | | | | | 480 | |
| CCT | TGT | GAA | GAA | TGG | AGA | AGT | GTG | GAG | GAC | TTC | CAG | GGA | GGA | AAT | AAA | 1488 |
| Pro | Cys | Glu | Glu | Trp | Arg | Ser | Val | Glu | Asp | Phe | Gln | Gly | Gly | Asn | Lys | |
| | | | | 485 | | | | | 490 | | | | | 495 | | |
| ATT | GAA | GTT | AAT | AAA | AAT | CAA | TTT | GCT | CTA | ATT | GAA | GGA | AAA | AAC | AAA | 1536 |
| Ile | Glu | Val | Asn | Lys | Asn | Gln | Phe | Ala | Leu | Ile | Glu | Gly | Lys | Asn | Lys | |
| | | | | 500 | | | | | 505 | | | | | 510 | | |

| | | | | | | | | | | | | | | | | |
|---|---|---|---|---|---|---|---|---|---|---|---|---|---|---|---|---|
| ACT | GTA | AGT | ACC | CTT | GTT | ATC | CAA | GCG | GCA | AAT | GTG | TCA | GCT | TTG | TAC | 1584 |
| Thr | Val | Ser | Thr | Leu | Val | Ile | Gln | Ala | Ala | Asn | Val | Ser | Ala | Leu | Tyr | |
| | | 515 | | | | | 520 | | | | | 525 | | | | |
| AAA | TGT | GAA | GCG | GTC | AAC | AAA | GTC | GGG | AGA | GGA | GAG | AGG | GTG | ATC | TCC | 1632 |
| Lys | Cys | Glu | Ala | Val | Asn | Lys | Val | Gly | Arg | Gly | Glu | Arg | Val | Ile | Ser | |
| 530 | | | | | 535 | | | | | 540 | | | | | | |
| TTC | CAC | GTG | ACC | AGG | GGT | CCT | GAA | ATT | ACT | TTG | CAA | CCT | GAC | ATG | CAG | 1680 |
| Phe | His | Val | Thr | Arg | Gly | Pro | Glu | Ile | Thr | Leu | Gln | Pro | Asp | Met | Gln | |
| 545 | | | | | 550 | | | | | 555 | | | | | 560 | |
| CCC | ACT | GAG | CAG | GAG | AGC | GTG | TCT | TTG | TGG | TGC | ACT | GCA | GAC | AGA | TCT | 1728 |
| Pro | Thr | Glu | Gln | Glu | Ser | Val | Ser | Leu | Trp | Cys | Thr | Ala | Asp | Arg | Ser | |
| | | | | 565 | | | | | 570 | | | | | 575 | | |
| ACG | TTT | GAG | AAC | CTC | ACA | TGG | TAC | AAG | CTT | GGC | CCA | CAG | CCT | CTG | CCA | 1776 |
| Thr | Phe | Glu | Asn | Leu | Thr | Trp | Tyr | Lys | Leu | Gly | Pro | Gln | Pro | Leu | Pro | |
| | | | 580 | | | | | 585 | | | | | 590 | | | |
| ATC | CAT | GTG | GGA | GAG | TTG | CCC | ACA | CCT | GTT | TGC | AAG | AAC | TTG | GAT | ACT | 1824 |
| Ile | His | Val | Gly | Glu | Leu | Pro | Thr | Pro | Val | Cys | Lys | Asn | Leu | Asp | Thr | |
| | | 595 | | | | | 600 | | | | | 605 | | | | |
| CTT | TGG | AAA | TTG | AAT | GCC | ACC | ATG | TTC | TCT | AAT | AGC | ACA | AAT | GAC | ATT | 1872 |
| Leu | Trp | Lys | Leu | Asn | Ala | Thr | Met | Phe | Ser | Asn | Ser | Thr | Asn | Asp | Ile | |
| | 610 | | | | | 615 | | | | | 620 | | | | | |
| TTG | ATC | ATG | GAG | CTT | AAG | AAT | GCA | TCC | TTG | CAG | GAC | CAA | GGA | GAC | TAT | 1920 |
| Leu | Ile | Met | Glu | Leu | Lys | Asn | Ala | Ser | Leu | Gln | Asp | Gln | Gly | Asp | Tyr | |
| 625 | | | | | 630 | | | | | 635 | | | | | 640 | |
| GTC | TGC | CTT | GCT | CAA | GAC | AGG | AAG | ACC | AAG | AAA | AGA | CAT | TGC | GTG | GTC | 1968 |
| Val | Cys | Leu | Ala | Gln | Asp | Arg | Lys | Thr | Lys | Lys | Arg | His | Cys | Val | Val | |
| | | | | 645 | | | | | 650 | | | | | 655 | | |
| AGG | CAG | CTC | ACA | GTC | CTA | GAG | CGT | GTG | GCA | CCC | ACG | ATC | ACA | GGA | AAC | 2016 |
| Arg | Gln | Leu | Thr | Val | Leu | Glu | Arg | Val | Ala | Pro | Thr | Ile | Thr | Gly | Asn | |
| | | | 660 | | | | | 665 | | | | | 670 | | | |
| CTG | GAG | AAT | CAG | ACG | ACA | AGT | ATT | GGG | GAA | AGC | ATC | GAA | GTC | TCA | TGC | 2064 |
| Leu | Glu | Asn | Gln | Thr | Thr | Ser | Ile | Gly | Glu | Ser | Ile | Glu | Val | Ser | Cys | |
| | | 675 | | | | | 680 | | | | | 685 | | | | |
| ACG | GCA | TCT | GGG | AAT | CCC | CCT | CCA | CAG | ATC | ATG | TGG | TTT | AAA | GAT | AAT | 2112 |
| Thr | Ala | Ser | Gly | Asn | Pro | Pro | Pro | Gln | Ile | Met | Trp | Phe | Lys | Asp | Asn | |
| 690 | | | | | 695 | | | | | 700 | | | | | | |
| GAG | ACC | CTT | GTA | GAA | GAC | TCA | GGC | ATT | GTA | TTG | AAG | GAT | GGG | AAC | CGG | 2160 |
| Glu | Thr | Leu | Val | Glu | Asp | Ser | Gly | Ile | Val | Leu | Lys | Asp | Gly | Asn | Arg | |
| 705 | | | | | 710 | | | | | 715 | | | | | 720 | |
| AAC | CTC | ACT | ATC | CGC | AGA | GTG | AGG | AAG | GAG | GAC | GAA | GGC | CTC | TAC | ACC | 2208 |
| Asn | Leu | Thr | Ile | Arg | Arg | Val | Arg | Lys | Glu | Asp | Glu | Gly | Leu | Tyr | Thr | |
| | | | | 725 | | | | | 730 | | | | | 735 | | |
| TGC | CAG | GCA | TGC | AGT | GTT | CTT | GGC | TGT | GCA | AAA | GTG | GAG | GCA | TTT | TTC | 2256 |
| Cys | Gln | Ala | Cys | Ser | Val | Leu | Gly | Cys | Ala | Lys | Val | Glu | Ala | Phe | Phe | |
| | | | 740 | | | | | 745 | | | | | 750 | | | |
| ATA | ATA | GAA | GGT | GCC | CAG | GAA | AAG | ACG | AAC | TTG | GAA | ATC | ATT | ATT | CTA | 2304 |
| Ile | Ile | Glu | Gly | Ala | Gln | Glu | Lys | Thr | Asn | Leu | Glu | Ile | Ile | Ile | Leu | |
| | | 755 | | | | | 760 | | | | | 765 | | | | |
| GTA | GGC | ACG | ACG | GTG | ATT | GCC | ATG | TTC | TTC | TGG | CTA | CTT | CTT | GTC | ATC | 2352 |
| Val | Gly | Thr | Thr | Val | Ile | Ala | Met | Phe | Phe | Trp | Leu | Leu | Leu | Val | Ile | |
| | 770 | | | | | 775 | | | | | 780 | | | | | |
| ATC | CTA | GGG | ACC | GTT | AAG | CGG | GCC | AAT | GGA | GGG | GAA | CTG | AAG | ACA | GGC | 2400 |
| Ile | Leu | Gly | Thr | Val | Lys | Arg | Ala | Asn | Gly | Gly | Glu | Leu | Lys | Thr | Gly | |
| 785 | | | | | 790 | | | | | 795 | | | | | 800 | |
| TAC | TTG | TCC | ATC | GTC | ATG | GAT | CCA | GAT | GAA | CTC | CCA | TTG | GAT | GAA | CAT | 2448 |
| Tyr | Leu | Ser | Ile | Val | Met | Asp | Pro | Asp | Glu | Leu | Pro | Leu | Asp | Glu | His | |
| | | | | 805 | | | | | 810 | | | | | 815 | | |
| TGT | GAA | CGA | CTG | CCT | TAT | GAT | GCC | AGC | AAA | TGG | GAA | TTC | CCC | AGA | GAC | 2496 |
| Cys | Glu | Arg | Leu | Pro | Tyr | Asp | Ala | Ser | Lys | Trp | Glu | Phe | Pro | Arg | Asp | |
| | | | 820 | | | | | 825 | | | | | 830 | | | |

| | | | | | | | | | | | | | | | | |
|---|---|---|---|---|---|---|---|---|---|---|---|---|---|---|---|---|
| CGG | CTG | AAC | CTA | GGT | AAG | CCT | CTT | GGC | CGT | GGT | GCC | TTT | GGC | CAA | GAG | 2544 |
| Arg | Leu | Asn 835 | Leu | Gly | Lys | Pro 840 | Leu | Gly | Arg | Gly | Ala 845 | Phe | Gly | Gln | Glu | |
| ATT | GAA | GCA | GAT | GCC | TTT | GGA | ATT | GAC | AAG | ACA | GCA | ACT | TGC | AGG | ACA | 2592 |
| Ile | Glu 850 | Ala | Asp | Ala | Phe | Gly 855 | Ile | Asp | Lys | Thr | Ala 860 | Thr | Cys | Arg | Thr | |
| GTA | GCA | GTC | AAA | ATG | TTG | AAA | GAA | GGA | GCA | ACA | CAC | AGT | GAG | CAT | CGA | 2640 |
| Val 865 | Ala | Val | Lys | Met | Leu 870 | Lys | Glu | Gly | Ala | Thr 875 | His | Ser | Glu | His | Arg 880 | |
| GCT | CTC | ATG | TCT | GAA | CTC | AAG | ATC | CTC | ATT | CAT | ATT | GGT | CAC | CAT | CTC | 2688 |
| Ala | Leu | Met | Ser | Glu 885 | Leu | Lys | Ile | Leu | Ile 890 | His | Ile | Gly | His | His 895 | Leu | |
| AAT | GTG | GTC | AAC | CTT | CTA | GGT | GCC | TGT | ACC | AAG | CCA | GGA | GGG | CCA | CTC | 2736 |
| Asn | Val | Val | Asn 900 | Leu | Leu | Gly | Ala | Cys 905 | Thr | Lys | Pro | Gly | Gly 910 | Pro | Leu | |
| ATG | GTG | ATT | GTG | GAA | TTC | TGC | AAA | TTT | GGA | AAC | CTG | TCC | ACT | TAC | CTG | 2784 |
| Met | Val | Ile 915 | Val | Glu | Phe | Cys | Lys 920 | Phe | Gly | Asn | Leu | Ser 925 | Thr | Tyr | Leu | |
| AGG | AGC | AAG | AGA | AAT | GAA | TTT | GTC | CCC | TAC | AAG | ACC | AAA | GGG | GCA | CGA | 2832 |
| Arg | Ser | Lys 930 | Arg | Asn | Glu | Phe | Val 935 | Pro | Tyr | Lys | Thr | Lys 940 | Gly | Ala | Arg | |
| TTC | CGT | CAA | GGG | AAA | GAC | TAC | GTT | GGA | GCA | ATC | CCT | GTG | GAT | CTG | AAA | 2880 |
| Phe 945 | Arg | Gln | Gly | Lys | Asp 950 | Tyr | Val | Gly | Ala | Ile 955 | Pro | Val | Asp | Leu | Lys 960 | |
| CGG | CGC | TTG | GAC | AGC | ATC | ACC | AGT | AGC | CAG | AGC | TCA | GCC | AGC | TCT | GGA | 2928 |
| Arg | Arg | Leu | Asp | Ser 965 | Ile | Thr | Ser | Ser | Gln 970 | Ser | Ser | Ala | Ser | Ser 975 | Gly | |
| TTT | GTG | GAG | GAG | AAG | TCC | CTC | AGT | GAT | GTA | GAA | GAA | GAG | GAA | GCT | CCT | 2976 |
| Phe | Val | Glu | Glu 980 | Lys | Ser | Leu | Ser | Asp 985 | Val | Glu | Glu | Glu | Glu 990 | Ala | Pro | |
| GAA | GAT | CTG | TAT | AAG | GAC | TTC | CTG | ACC | TTG | GAG | CAT | CTC | ATC | TGT | TAC | 3024 |
| Glu | Asp | Leu | Tyr 995 | Lys | Asp | Phe | Leu | Thr 1000 | Leu | Glu | His | Leu | Ile 1005 | Cys | Tyr | |
| AGC | TTC | CAA | GTG | GCT | AAG | GGC | ATG | GAG | TTC | TTG | GCA | TCG | CGA | AAG | TGT | 3072 |
| Ser | Phe | Gln 1010 | Val | Ala | Lys | Gly | Met 1015 | Glu | Phe | Leu | Ala | Ser 1020 | Arg | Lys | Cys | |
| ATC | CAC | AGG | GAC | CTG | GCG | GCA | CGA | AAT | ATC | CTC | TTA | TCG | GAG | AAG | AAC | 3120 |
| Ile | His | Arg | Asp 1025 | Leu | Ala | Ala | Arg 1030 | Asn | Ile | Leu | Leu | Ser 1035 | Glu | Lys | Asn 1040 | |
| GTG | GTT | AAA | ATC | TGT | GAC | TTT | GGC | TTG | GCC | CGG | GAT | ATT | TAT | AAA | GAT | 3168 |
| Val | Val | Lys | Ile | Cys 1045 | Asp | Phe | Gly | Leu | Ala 1050 | Arg | Asp | Ile | Tyr | Lys 1055 | Asp | |
| CCA | GAT | TAT | GTC | AGA | AAA | GGA | GAT | GCT | CGC | CTC | CCT | TTG | AAA | TGG | ATG | 3216 |
| Pro | Asp | Tyr | Val 1060 | Arg | Lys | Gly | Asp | Ala 1065 | Arg | Leu | Pro | Leu | Lys 1070 | Trp | Met | |
| GCC | CCA | GAA | ACA | ATT | TTT | GAC | AGA | GTG | TAC | ACA | ATC | CAG | AGT | GAC | GTC | 3264 |
| Ala | Pro | Glu | Thr 1075 | Ile | Phe | Asp | Arg | Val 1080 | Tyr | Thr | Ile | Gln | Ser 1085 | Asp | Val | |
| TGG | TCT | TTT | GGT | GTT | TTG | CTG | TGG | GAA | ATA | TTT | TCC | TTA | GGT | GCT | TCT | 3312 |
| Trp | Ser | Phe | Gly 1090 | Val | Leu | Leu | Trp | Glu 1095 | Ile | Phe | Ser | Leu | Gly 1100 | Ala | Ser | |
| CCA | TAT | CCT | GGG | GTA | AAG | ATT | GAT | GAA | GAA | TTT | TGT | AGG | CGA | TTG | AAA | 3360 |
| Pro | Tyr | Pro 1105 | Gly | Val | Lys | Ile | Asp 1110 | Glu | Glu | Phe | Cys | Arg 1115 | Arg | Leu | Lys 1120 | |
| GAA | GGA | ACT | AGA | ATG | AGG | GCC | CCT | GAT | TAT | ACT | ACA | CCA | GAA | ATG | TAC | 3408 |
| Glu | Gly | Thr | Arg | Met 1125 | Arg | Ala | Pro | Asp | Tyr 1130 | Thr | Thr | Pro | Glu | Met 1135 | Tyr | |
| CAG | ACC | ATG | CTG | GAC | TGC | TGG | CAC | GGG | GAG | CCC | AGT | CAG | AGA | CCC | ACG | 3456 |
| Gln | Thr | Met | Leu | Asp 1140 | Cys | Trp | His | Gly | Glu 1145 | Pro | Ser | Gln | Arg | Pro 1150 | Thr | |

-continued

| | | | | | | | | | | | | | | | | |
|---|---|---|---|---|---|---|---|---|---|---|---|---|---|---|---|---|
| TTT | TCA | GAG | TTG | GTG | GAA | CAT | TTG | GGA | AAT | CTC | TTG | CAA | GCT | AAT | GCT | 3504 |
| Phe | Ser | Glu | Leu | Val | Glu | His | Leu | Gly | Asn | Leu | Leu | Gln | Ala | Asn | Ala | |
| | | 1155 | | | | | 1160 | | | | | 1165 | | | | |
| CAG | CAG | GAT | GGC | AAA | GAC | TAC | ATT | GTT | CTT | CCG | ATA | TCA | GAG | ACT | TTG | 3552 |
| Gln | Gln | Asp | Gly | Lys | Asp | Tyr | Ile | Val | Leu | Pro | Ile | Ser | Glu | Thr | Leu | |
| | 1170 | | | | | 1175 | | | | | 1180 | | | | | |
| AGC | ATG | GAA | GAG | GAT | TCT | GGA | CTC | TCT | CTG | CCT | ACC | TCA | CCT | GTT | TCC | 3600 |
| Ser | Met | Glu | Glu | Asp | Ser | Gly | Leu | Ser | Leu | Pro | Thr | Ser | Pro | Val | Ser | |
| 1185 | | | | | 1190 | | | | | 1195 | | | | | 1200 | |
| TGT | ATG | GAG | GAG | GAG | GAA | GTA | TGT | GAC | CCC | AAA | TTC | CAT | TAT | GAC | AAC | 3648 |
| Cys | Met | Glu | Glu | Glu | Glu | Val | Cys | Asp | Pro | Lys | Phe | His | Tyr | Asp | Asn | |
| | | | | 1205 | | | | | 1210 | | | | | 1215 | | |
| ACA | GCA | GGA | ATC | AGT | CAG | TAT | CTG | CAG | AAC | AGT | AAG | CGA | AAG | AGC | CGG | 3696 |
| Thr | Ala | Gly | Ile | Ser | Gln | Tyr | Leu | Gln | Asn | Ser | Lys | Arg | Lys | Ser | Arg | |
| | | | 1220 | | | | | 1225 | | | | | 1230 | | | |
| CCT | GTG | AGT | GTA | AAA | ACA | TTT | GAA | GAT | ATC | CCG | TTA | GAA | GAA | CCA | GAA | 3744 |
| Pro | Val | Ser | Val | Lys | Thr | Phe | Glu | Asp | Ile | Pro | Leu | Glu | Glu | Pro | Glu | |
| | | | 1235 | | | | | 1240 | | | | | 1245 | | | |
| GTA | AAA | GTA | ATC | CCA | GAT | GAC | AAC | CAG | ACG | GAC | AGT | GGT | ATG | GTT | CTT | 3792 |
| Val | Lys | Val | Ile | Pro | Asp | Asp | Asn | Gln | Thr | Asp | Ser | Gly | Met | Val | Leu | |
| | | 1250 | | | | | 1255 | | | | | 1260 | | | | |
| GCC | TCA | GAA | GAG | CTG | AAA | ACT | TTG | GAA | GAC | AGA | ACC | AAA | TTA | TCT | CCA | 3840 |
| Ala | Ser | Glu | Glu | Leu | Lys | Thr | Leu | Glu | Asp | Arg | Thr | Lys | Leu | Ser | Pro | |
| 1265 | | | | | 1270 | | | | | 1275 | | | | | 1280 | |
| TCT | TTT | GGT | GGA | ATG | GTG | CCC | AGC | AAA | AGC | AGG | GAG | TCT | GTG | GCA | TCT | 3888 |
| Ser | Phe | Gly | Gly | Met | Val | Pro | Ser | Lys | Ser | Arg | Glu | Ser | Val | Ala | Ser | |
| | | | | 1285 | | | | | 1290 | | | | | 1295 | | |
| GAA | GGC | TCA | AAC | CAG | ACA | AGC | GGC | TAC | CAG | TCC | GGA | TAT | CAC | TCC | GAT | 3936 |
| Glu | Gly | Ser | Asn | Gln | Thr | Ser | Gly | Tyr | Gln | Ser | Gly | Tyr | His | Ser | Asp | |
| | | | 1300 | | | | | 1305 | | | | | 1310 | | | |
| GAC | ACA | GAC | ACC | ACC | GTG | TAC | TCC | AGT | GAG | GAA | GCA | GAA | CTT | TTA | AAG | 3984 |
| Asp | Thr | Asp | Thr | Thr | Val | Tyr | Ser | Ser | Glu | Glu | Ala | Glu | Leu | Leu | Lys | |
| | | 1315 | | | | | 1320 | | | | | 1325 | | | | |
| CTG | ATA | GAG | ATT | GGA | GTG | CAA | ACC | GGT | AGC | ACA | GCC | CAG | ATT | CTC | CAG | 4032 |
| Leu | Ile | Glu | Ile | Gly | Val | Gln | Thr | Gly | Ser | Thr | Ala | Gln | Ile | Leu | Gln | |
| | | 1330 | | | | | 1335 | | | | | 1340 | | | | |
| CCT | GAC | ACG | GGG | ACC | ACA | CTG | AGC | TCT | CCT | CCT | GTT | TAAAAGGAAG | | | | 4078 |
| Pro | Asp | Thr | Gly | Thr | Thr | Leu | Ser | Ser | Pro | Pro | Val | | | | | |
| 1345 | | | | | 1350 | | | | | 1355 | | | | | | |

| | |
|---|---|
| CATCCACACC CCAACTCCCG GACATCACAT GAGAGGTCTG CTCAGATTTT GAAGTGTTGT | 4138 |
| TCTTTCCACC AGCAGGAAGT AGCCGCATTT GATTTTCATT TCGACAACAG AAAAAGGACC | 4198 |
| TCGGACTGCA GGGAGCCAGC TCTTCTAGGC TTGTGACC | 4236 |

( 2 ) INFORMATION FOR SEQ ID NO:8:

( i ) SEQUENCE CHARACTERISTICS:
        ( A ) LENGTH: 1356 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Glu | Ser | Lys | Val | Leu | Leu | Ala | Val | Ala | Leu | Trp | Leu | Cys | Val | Glu |
| 1 | | | | 5 | | | | | 10 | | | | | 15 | |
| Thr | Arg | Ala | Ala | Ser | Val | Gly | Leu | Pro | Ser | Val | Ser | Leu | Asp | Leu | Pro |
| | | | 20 | | | | | 25 | | | | | 30 | | |
| Arg | Leu | Ser | Ile | Gln | Lys | Asp | Ile | Leu | Thr | Ile | Lys | Ala | Asn | Thr | Thr |
| | | 35 | | | | | 40 | | | | | 45 | | | |
| Leu | Gln | Ile | Thr | Cys | Arg | Gly | Gln | Arg | Asp | Leu | Asp | Trp | Leu | Trp | Pro |

```
                    50                         55                          60
Asn  Asn  Gln  Ser  Gly  Ser  Glu  Gln  Arg  Val  Glu  Val  Thr  Glu  Cys  Ser
 65                      70                        75                          80

Asp  Gly  Leu  Phe  Cys  Lys  Thr  Leu  Thr  Ile  Pro  Lys  Val  Ile  Gly  Asn
                         85                        90                      95

Asp  Thr  Gly  Ala  Tyr  Lys  Cys  Phe  Tyr  Arg  Glu  Thr  Asp  Leu  Ala  Ser
                    100                      105                 110

Val  Ile  Tyr  Val  Tyr  Val  Gln  Asp  Tyr  Arg  Ser  Pro  Phe  Ile  Ala  Ser
          115                      120                      125

Val  Ser  Asp  Gln  His  Gly  Val  Val  Tyr  Ile  Thr  Glu  Asn  Lys  Asn  Lys
          130                      135                      140

Thr  Val  Val  Ile  Pro  Cys  Leu  Gly  Ser  Ile  Ser  Asn  Leu  Asn  Val  Ser
145                      150                      155                          160

Leu  Cys  Ala  Arg  Tyr  Pro  Glu  Lys  Arg  Phe  Val  Pro  Asp  Gly  Asn  Arg
                    165                      170                          175

Ile  Ser  Trp  Asp  Ser  Lys  Lys  Gly  Phe  Thr  Ile  Pro  Ser  Tyr  Met  Ile
                    180                      185                      190

Ser  Tyr  Ala  Gly  Met  Val  Phe  Cys  Glu  Ala  Lys  Ile  Asn  Asp  Glu  Ser
          195                      200                      205

Tyr  Gln  Ser  Ile  Met  Tyr  Ile  Val  Val  Val  Val  Gly  Tyr  Arg  Ile  Tyr
     210                      215                      220

Asp  Val  Val  Leu  Ser  Pro  Ser  His  Gly  Ile  Glu  Leu  Ser  Val  Gly  Glu
225                      230                      235                          240

Lys  Leu  Val  Leu  Asn  Cys  Thr  Ala  Arg  Thr  Glu  Leu  Asn  Val  Gly  Ile
                    245                      250                          255

Asp  Phe  Asn  Trp  Glu  Tyr  Pro  Ser  Ser  Lys  His  Gln  His  Lys  Lys  Leu
                    260                      265                      270

Val  Asn  Arg  Asp  Leu  Lys  Thr  Gln  Ser  Gly  Ser  Glu  Met  Lys  Lys  Phe
          275                      280                      285

Leu  Ser  Thr  Leu  Thr  Ile  Asp  Gly  Val  Thr  Arg  Ser  Asp  Gln  Gly  Leu
     290                      295                      300

Tyr  Thr  Cys  Ala  Ala  Ser  Ser  Gly  Leu  Met  Thr  Lys  Lys  Asn  Ser  Thr
305                      310                      315                          320

Phe  Val  Arg  Val  His  Glu  Lys  Pro  Phe  Val  Ala  Phe  Gly  Ser  Gly  Met
                    325                      330                      335

Glu  Ser  Leu  Val  Glu  Ala  Thr  Val  Gly  Glu  Arg  Val  Arg  Ile  Pro  Ala
               340                      345                      350

Lys  Tyr  Leu  Gly  Tyr  Pro  Pro  Pro  Glu  Ile  Lys  Trp  Tyr  Lys  Asn  Gly
          355                      360                      365

Ile  Pro  Leu  Glu  Ser  Asn  His  Thr  Ile  Lys  Ala  Gly  His  Val  Leu  Thr
     370                      375                      380

Ile  Met  Glu  Val  Ser  Glu  Arg  Asp  Thr  Gly  Asn  Tyr  Thr  Val  Ile  Leu
385                      390                      395                          400

Thr  Asn  Pro  Ile  Ser  Lys  Glu  Lys  Gln  Ser  His  Val  Val  Ser  Leu  Val
                    405                      410                      415

Val  Tyr  Val  Pro  Pro  Gln  Ile  Gly  Glu  Lys  Ser  Leu  Ile  Ser  Pro  Val
               420                      425                      430

Asp  Ser  Tyr  Gln  Tyr  Gly  Thr  Thr  Gln  Thr  Leu  Thr  Cys  Thr  Val  Tyr
          435                      440                      445

Ala  Ile  Pro  Pro  Pro  His  His  Ile  His  Trp  Tyr  Trp  Gln  Leu  Glu  Glu
     450                      455                      460

Glu  Cys  Ala  Asn  Glu  Pro  Ser  Gln  Ala  Val  Ser  Val  Thr  Asn  Pro  Tyr
465                      470                      475                          480
```

```
Pro  Cys  Glu  Glu  Trp  Arg  Ser  Val  Glu  Asp  Phe  Gln  Gly  Gly  Asn  Lys
               485                     490                         495

Ile  Glu  Val  Asn  Lys  Asn  Gln  Phe  Ala  Leu  Ile  Glu  Gly  Lys  Asn  Lys
               500                     505                         510

Thr  Val  Ser  Thr  Leu  Val  Ile  Gln  Ala  Ala  Asn  Val  Ser  Ala  Leu  Tyr
               515                     520                         525

Lys  Cys  Glu  Ala  Val  Asn  Lys  Val  Gly  Arg  Gly  Glu  Arg  Val  Ile  Ser
530                           535                     540

Phe  His  Val  Thr  Arg  Gly  Pro  Glu  Ile  Thr  Leu  Gln  Pro  Asp  Met  Gln
545                      550                     555                         560

Pro  Thr  Glu  Gln  Glu  Ser  Val  Ser  Leu  Trp  Cys  Thr  Ala  Asp  Arg  Ser
               565                     570                         575

Thr  Phe  Glu  Asn  Leu  Thr  Trp  Tyr  Lys  Leu  Gly  Pro  Gln  Pro  Leu  Pro
               580                     585                         590

Ile  His  Val  Gly  Glu  Leu  Pro  Thr  Pro  Val  Cys  Lys  Asn  Leu  Asp  Thr
               595                     600                         605

Leu  Trp  Lys  Leu  Asn  Ala  Thr  Met  Phe  Ser  Asn  Ser  Thr  Asn  Asp  Ile
     610                      615                     620

Leu  Ile  Met  Glu  Leu  Lys  Asn  Ala  Ser  Leu  Gln  Asp  Gln  Gly  Asp  Tyr
625                           630                     635                         640

Val  Cys  Leu  Ala  Gln  Asp  Arg  Lys  Thr  Lys  Lys  Arg  His  Cys  Val  Val
                    645                     650                         655

Arg  Gln  Leu  Thr  Val  Leu  Glu  Arg  Val  Ala  Pro  Thr  Ile  Thr  Gly  Asn
               660                     665                         670

Leu  Glu  Asn  Gln  Thr  Thr  Ser  Ile  Gly  Glu  Ser  Ile  Glu  Val  Ser  Cys
               675                     680                         685

Thr  Ala  Ser  Gly  Asn  Pro  Pro  Pro  Gln  Ile  Met  Trp  Phe  Lys  Asp  Asn
     690                      695                     700

Glu  Thr  Leu  Val  Glu  Asp  Ser  Gly  Ile  Val  Leu  Lys  Asp  Gly  Asn  Arg
705                           710                     715                         720

Asn  Leu  Thr  Ile  Arg  Arg  Val  Arg  Lys  Glu  Asp  Glu  Gly  Leu  Tyr  Thr
                    725                     730                         735

Cys  Gln  Ala  Cys  Ser  Val  Leu  Gly  Cys  Ala  Lys  Val  Glu  Ala  Phe  Phe
               740                     745                         750

Ile  Ile  Glu  Gly  Ala  Gln  Glu  Lys  Thr  Asn  Leu  Glu  Ile  Ile  Ile  Leu
               755                     760                         765

Val  Gly  Thr  Thr  Val  Ile  Ala  Met  Phe  Phe  Trp  Leu  Leu  Leu  Val  Ile
     770                      775                     780

Ile  Leu  Gly  Thr  Val  Lys  Arg  Ala  Asn  Gly  Gly  Glu  Leu  Lys  Thr  Gly
785                           790                     795                         800

Tyr  Leu  Ser  Ile  Val  Met  Asp  Pro  Asp  Glu  Leu  Pro  Leu  Asp  Glu  His
                    805                     810                         815

Cys  Glu  Arg  Leu  Pro  Tyr  Asp  Ala  Ser  Lys  Trp  Glu  Phe  Pro  Arg  Asp
               820                     825                         830

Arg  Leu  Asn  Leu  Gly  Lys  Pro  Leu  Gly  Arg  Gly  Ala  Phe  Gly  Gln  Glu
               835                     840                         845

Ile  Glu  Ala  Asp  Ala  Phe  Gly  Ile  Asp  Lys  Thr  Ala  Thr  Cys  Arg  Thr
     850                      855                     860

Val  Ala  Val  Lys  Met  Leu  Lys  Glu  Gly  Ala  Thr  His  Ser  Glu  His  Arg
865                           870                     875                         880

Ala  Leu  Met  Ser  Glu  Leu  Lys  Ile  Leu  Ile  His  Ile  Gly  His  His  Leu
                    885                     890                         895

Asn  Val  Val  Asn  Leu  Leu  Gly  Ala  Cys  Thr  Lys  Pro  Gly  Gly  Pro  Leu
                    900                     905                         910
```

-continued

```
Met  Val  Ile  Val  Glu  Phe  Cys  Lys  Phe  Gly  Asn  Leu  Ser  Thr  Tyr  Leu
          915                      920                     925

Arg  Ser  Lys  Arg  Asn  Glu  Phe  Val  Pro  Tyr  Lys  Thr  Lys  Gly  Ala  Arg
          930                      935                     940

Phe  Arg  Gln  Gly  Lys  Asp  Tyr  Val  Gly  Ala  Ile  Pro  Val  Asp  Leu  Lys
945                           950                     955                      960

Arg  Arg  Leu  Asp  Ser  Ile  Thr  Ser  Ser  Gln  Ser  Ser  Ala  Ser  Ser  Gly
               965                           970                     975

Phe  Val  Glu  Glu  Lys  Ser  Leu  Ser  Asp  Val  Glu  Glu  Glu  Glu  Ala  Pro
               980                           985                     990

Glu  Asp  Leu  Tyr  Lys  Asp  Phe  Leu  Thr  Leu  Glu  His  Leu  Ile  Cys  Tyr
               995                          1000                    1005

Ser  Phe  Gln  Val  Ala  Lys  Gly  Met  Glu  Phe  Leu  Ala  Ser  Arg  Lys  Cys
              1010                          1015                    1020

Ile  His  Arg  Asp  Leu  Ala  Ala  Arg  Asn  Ile  Leu  Leu  Ser  Glu  Lys  Asn
1025                          1030                    1035                   1040

Val  Val  Lys  Ile  Cys  Asp  Phe  Gly  Leu  Ala  Arg  Asp  Ile  Tyr  Lys  Asp
                    1045                    1050                    1055

Pro  Asp  Tyr  Val  Arg  Lys  Gly  Asp  Ala  Arg  Leu  Pro  Leu  Lys  Trp  Met
                    1060                    1065                    1070

Ala  Pro  Glu  Thr  Ile  Phe  Asp  Arg  Val  Tyr  Thr  Ile  Gln  Ser  Asp  Val
               1075                         1080                    1085

Trp  Ser  Phe  Gly  Val  Leu  Leu  Trp  Glu  Ile  Phe  Ser  Leu  Gly  Ala  Ser
               1090                         1095                    1100

Pro  Tyr  Pro  Gly  Val  Lys  Ile  Asp  Glu  Glu  Phe  Cys  Arg  Arg  Leu  Lys
1105                          1110                    1115                   1120

Glu  Gly  Thr  Arg  Met  Arg  Ala  Pro  Asp  Tyr  Thr  Thr  Pro  Glu  Met  Tyr
                    1125                    1130                          1135

Gln  Thr  Met  Leu  Asp  Cys  Trp  His  Gly  Glu  Pro  Ser  Gln  Arg  Pro  Thr
               1140                         1145                    1150

Phe  Ser  Glu  Leu  Val  Glu  His  Leu  Gly  Asn  Leu  Leu  Gln  Ala  Asn  Ala
               1155                         1160                    1165

Gln  Gln  Asp  Gly  Lys  Asp  Tyr  Ile  Val  Leu  Pro  Ile  Ser  Glu  Thr  Leu
          1170                    1175                    1180

Ser  Met  Glu  Glu  Asp  Ser  Gly  Leu  Ser  Leu  Pro  Thr  Ser  Pro  Val  Ser
1185                     1190                          1195                  1200

Cys  Met  Glu  Glu  Glu  Glu  Val  Cys  Asp  Pro  Lys  Phe  His  Tyr  Asp  Asn
                    1205                    1210                    1215

Thr  Ala  Gly  Ile  Ser  Gln  Tyr  Leu  Gln  Asn  Ser  Lys  Arg  Lys  Ser  Arg
                    1220                    1225                    1230

Pro  Val  Ser  Val  Lys  Thr  Phe  Glu  Asp  Ile  Pro  Leu  Glu  Glu  Pro  Glu
               1235                    1240                     1245

Val  Lys  Val  Ile  Pro  Asp  Asp  Asn  Gln  Thr  Asp  Ser  Gly  Met  Val  Leu
          1250                    1255                     1260

Ala  Ser  Glu  Glu  Leu  Lys  Thr  Leu  Glu  Asp  Arg  Thr  Lys  Leu  Ser  Pro
1265                     1270                          1275                  1280

Ser  Phe  Gly  Gly  Met  Val  Pro  Ser  Lys  Ser  Arg  Glu  Ser  Val  Ala  Ser
                    1285                    1290                          1295

Glu  Gly  Ser  Asn  Gln  Thr  Ser  Gly  Tyr  Gln  Ser  Gly  Tyr  His  Ser  Asp
               1300                         1305                    1310

Asp  Thr  Asp  Thr  Thr  Val  Tyr  Ser  Ser  Glu  Glu  Ala  Glu  Leu  Leu  Lys
               1315                         1320                    1325

Leu  Ile  Glu  Ile  Gly  Val  Gln  Thr  Gly  Ser  Thr  Ala  Gln  Ile  Leu  Gln
```

|  | | 1330 | | | 1335 | | | | 1340 | |  |  |  |
|---|---|---|---|---|---|---|---|---|---|---|---|---|---|

Pro Asp Thr Gly Thr Thr Leu Ser Ser Pro Pro Val
1345             1350                 1355

( 2 ) INFORMATION FOR SEQ ID NO:9:

( i ) SEQUENCE CHARACTERISTICS:
        ( A ) LENGTH: 433 amino acids
        ( B ) TYPE: amino acid
        ( D ) TOPOLOGY: linear ( i i ) MOLECULE TYPE: peptide ( x ) PUBLICATION INFORMATION:
        ( A ) AUTHORS: Yarden, Y., et al.
        ( C ) JOURNAL: EMBO J.
        ( D ) VOLUME: 6
        ( F ) PAGES: 3341-3351
        ( G ) DATE: 1987

( x i ) SEQUENCE DESCRIPTION: SEQ ID NO:9:

Leu Thr Tyr Lys Tyr Leu Gln Lys Pro Met Tyr Glu Val Gln Trp Lys
1               5                   10                  15

Val Val Glu Glu Ile Asn Gly Asn Asn Tyr Val Tyr Ile Asp Pro Thr
                20                  25                  30

Gln Leu Pro Tyr Asp His Lys Trp Glu Phe Pro Arg Asn Arg Leu Ser
            35                  40                  45

Phe Gly Lys Thr Leu Gly Ala Gly Ala Phe Gly Lys Val Val Ala Glu
        50                  55                  60

Thr Ala Tyr Gly Leu Ile Lys Ser Asp Ala Ala Met Thr Val Ala Val
65                      70                  75                  80

Lys Met Leu Lys Pro Ser Ala His Leu Thr Glu Arg Glu Ala Leu Met
                85                  90                  95

Ser Glu Leu Lys Val Leu Ser Tyr Leu Gly Asn His Met Asn Ile Val
                100                 105                 110

Asn Leu Leu Gly Ala Cys Thr Ile Gly Gly Pro Thr Leu Val Ile Thr
            115                 120                 125

Glu Tyr Cys Cys Tyr Gly Asp Leu Leu Asn Phe Leu Arg Arg Lys Arg
    130                 135                 140

Asp Ser Phe Ile Cys Ser Lys Gln Glu Asp His Ala Glu Ala Ala Leu
145                 150                 155                 160

Tyr Lys Asn Leu Leu His Ser Lys Glu Ser Ser Cys Ser Asp Ser Thr
                165                 170                 175

Asn Glu Tyr Met Asp Met Lys Pro Gly Val Ser Tyr Val Val Pro Thr
            180                 185                 190

Lys Ala Asp Lys Arg Arg Ser Val Arg Ile Gly Ser Tyr Ile Glu Arg
        195                 200                 205

Asp Val Thr Pro Ala Ile Met Glu Asp Asp Glu Leu Ala Leu Asp Leu
    210                 215                 220

Glu Asp Leu Leu Ser Phe Ser Tyr Gln Val Lys Gly Met Ala Phe Leu
225                 230                 235                 240

Ala Ser Lys Asn Cys Ile His Arg Asp Leu Ala Ala Arg Asn Ile Leu
                245                 250                 255

Leu Thr His Gly Arg Ile Thr Lys Ile Cys Asp Phe Gly Leu Ala Arg
            260                 265                 270

Asp Ile Lys Asn Asp Ser Asn Tyr Val Val Lys Gly Asn Ala Arg Leu
        275                 280                 285

Pro Val Lys Val Met Ala Pro Glu Ser Ile Phe Asn Cys Val Tyr Thr
    290                 295                 300

|  |  |  |  |  |  |  |  |  |  |  |  |  |  |  |  |
|---|---|---|---|---|---|---|---|---|---|---|---|---|---|---|---|
| Glu | Glu | Ser | Asp | Val | Trp | Ser | Tyr | Gly | Ile | Phe | Leu | Trp | Glu | Leu | Phe |
| 305 |  |  |  |  | 310 |  |  |  | 315 |  |  |  |  |  | 320 |
| Ser | Leu | Gly | Ser | Ser | Pro | Tyr | Pro | Gly | Met | Pro | Val | Lys | Ser | Lys | Phe |
|  |  |  |  | 325 |  |  |  |  | 330 |  |  |  |  | 335 |  |
| Tyr | Lys | Met | Ile | Lys | Glu | Gly | Phe | Arg | Met | Leu | Ser | Pro | Glu | His | Ala |
|  |  |  | 340 |  |  |  |  | 345 |  |  |  |  | 350 |  |  |
| Pro | Ala | Glu | Met | Tyr | Asp | Ile | Met | Lys | Thr | Cys | Trp | Asp | Ala | Asp | Pro |
|  |  | 355 |  |  |  |  | 360 |  |  |  |  | 365 |  |  |  |
| Leu | Lys | Arg | Pro | Thr | Phe | Lys | Gln | Ile | Val | Gln | Leu | Ile | Glu | Lys | Gln |
|  | 370 |  |  |  |  | 375 |  |  |  |  | 380 |  |  |  |  |
| Ile | Ser | Glu | Ser | Thr | Asn | His | Ile | Tyr | Ser | Asn | Leu | Ala | Asn | Cys | Ser |
| 385 |  |  |  |  | 390 |  |  |  |  | 395 |  |  |  |  | 400 |
| Pro | Asn | Arg | Gln | Lys | Pro | Val | Val | Asp | His | Ser | Val | Arg | Ile | Asn | Ser |
|  |  |  |  | 405 |  |  |  |  | 410 |  |  |  |  | 415 |  |
| Val | Gly | Ser | Thr | Ala | Ser | Ser | Ser | Gln | Pro | Leu | Leu | Val | His | Asp | Asp |
|  |  |  | 420 |  |  |  |  | 425 |  |  |  |  | 430 |  |  |
| Val |  |  |  |  |  |  |  |  |  |  |  |  |  |  |  |

( 2 ) INFORMATION FOR SEQ ID NO:10:

( i ) SEQUENCE CHARACTERISTICS:
        ( A ) LENGTH: 437 amino acids
        ( B ) TYPE: amino acid
        ( D ) TOPOLOGY: linear ( i i ) MOLECULE TYPE: peptide ( x ) PUBLICATION INFORMATION:
        ( A ) AUTHORS: Coussens, L., et al.
        ( C ) JOURNAL: Nature
        ( D ) VOLUME: 320
        ( F ) PAGES: 277-280
        ( G ) DATE: 1986

( x i ) SEQUENCE DESCRIPTION: SEQ ID NO:10:

|  |  |  |  |  |  |  |  |  |  |  |  |  |  |  |  |
|---|---|---|---|---|---|---|---|---|---|---|---|---|---|---|---|
| Leu | Leu | Tyr | Lys | Tyr | Lys | Gln | Lys | Pro | Lys | Tyr | Gln | Val | Arg | Trp | Lys |
| 1 |  |  |  | 5 |  |  |  |  | 10 |  |  |  |  | 15 |  |
| Ile | Ile | Glu | Ser | Tyr | Glu | Gly | Asn | Ser | Tyr | Thr | Phe | Ile | Asp | Pro | Thr |
|  |  |  | 20 |  |  |  |  | 25 |  |  |  |  | 30 |  |  |
| Gln | Leu | Pro | Tyr | Asn | Glu | Lys | Trp | Glu | Phe | Pro | Arg | Asn | Asn | Leu | Gln |
|  |  | 35 |  |  |  |  | 40 |  |  |  |  | 45 |  |  |  |
| Phe | Gly | Lys | Thr | Leu | Gly | Ala | Gly | Ala | Phe | Gly | Lys | Val | Val | Glu | Ala |
|  | 50 |  |  |  |  | 55 |  |  |  |  | 60 |  |  |  |  |
| Thr | Ala | Phe | Gly | Leu | Gly | Lys | Glu | Asp | Ala | Val | Leu | Lys | Val | Ala | Val |
| 65 |  |  |  |  | 70 |  |  |  |  | 75 |  |  |  |  | 80 |
| Lys | Met | Leu | Lys | Ser | Thr | Ala | His | Ala | Asp | Glu | Lys | Glu | Ala | Leu | Met |
|  |  |  |  | 85 |  |  |  |  | 90 |  |  |  |  | 95 |  |
| Ser | Glu | Leu | Lys | Ile | Met | Ser | His | Leu | Gly | Gln | His | Glu | Asn | Ile | Val |
|  |  |  | 100 |  |  |  |  | 105 |  |  |  |  | 110 |  |  |
| Asn | Leu | Leu | Gly | Ala | Cys | Thr | His | Gly | Gly | Pro | Val | Leu | Val | Ile | Thr |
|  |  | 115 |  |  |  |  | 120 |  |  |  |  | 125 |  |  |  |
| Glu | Tyr | Cys | Cys | Tyr | Gly | Asp | Leu | Leu | Asn | Phe | Leu | Arg | Arg | Lys | Ala |
|  | 130 |  |  |  |  | 135 |  |  |  |  | 140 |  |  |  |  |
| Glu | Ala | Met | Leu | Gly | Pro | Ser | Leu | Ser | Pro | Gly | Gln | Asp | Pro | Glu | Gly |
| 145 |  |  |  |  | 150 |  |  |  |  | 155 |  |  |  |  | 160 |
| Gly | Val | Asp | Tyr | Lys | Asn | Ile | His | Leu | Glu | Lys | Lys | Tyr | Val | Arg | Arg |
|  |  |  |  | 165 |  |  |  |  | 170 |  |  |  |  | 175 |  |
| Asp | Ser | Gly | Phe | Ser | Ser | Gln | Gly | Val | Asp | Thr | Tyr | Val | Glu | Met | Arg |

|     |     |     |     | 180 |     |     |     | 185 |     |     |     | 190 |     |     |
| --- | --- | --- | --- | --- | --- | --- | --- | --- | --- | --- | --- | --- | --- | --- |
| Pro | Val | Ser | Thr | Ser | Ser | Asn | Asp | Ser | Phe | Ser | Glu | Gln | Asp | Leu | Asp |
|     |     | 195 |     |     |     |     | 200 |     |     |     |     | 205 |     |     |     |
| Lys | Glu | Asp | Gly | Arg | Pro | Leu | Glu | Leu | Arg | Asp | Leu | Leu | His | Phe | Ser |
|     | 210 |     |     |     |     | 215 |     |     |     |     | 220 |     |     |     |     |
| Ser | Gln | Val | Ala | Gln | Gly | Met | Ala | Phe | Leu | Ala | Ser | Lys | Asn | Cys | Ile |
| 225 |     |     |     |     | 230 |     |     |     |     | 235 |     |     |     |     | 240 |
| His | Arg | Asp | Val | Ala | Ala | Arg | Asn | Val | Leu | Leu | Thr | Asn | Gly | His | Val |
|     |     |     |     | 245 |     |     |     |     | 250 |     |     |     |     | 255 |     |
| Ala | Lys | Ile | Gly | Asp | Phe | Gly | Leu | Ala | Arg | Asp | Ile | Met | Asn | Asp | Ser |
|     |     |     | 260 |     |     |     |     | 265 |     |     |     |     | 270 |     |     |
| Asn | Tyr | Ile | Val | Lys | Gly | Asn | Ala | Arg | Leu | Pro | Val | Lys | Trp | Met | Ala |
|     |     | 275 |     |     |     |     | 280 |     |     |     |     | 285 |     |     |     |
| Pro | Glu | Ser | Ile | Phe | Asp | Cys | Val | Tyr | Thr | Val | Gln | Ser | Asp | Val | Trp |
|     | 290 |     |     |     |     | 295 |     |     |     |     | 300 |     |     |     |     |
| Ser | Tyr | Gly | Ile | Leu | Leu | Trp | Glu | Ile | Phe | Ser | Leu | Gly | Leu | Asn | Pro |
| 305 |     |     |     |     | 310 |     |     |     |     | 315 |     |     |     |     | 320 |
| Tyr | Pro | Gly | Ile | Leu | Val | Asn | Ser | Lys | Phe | Tyr | Lys | Leu | Val | Lys | Asp |
|     |     |     |     | 325 |     |     |     |     | 330 |     |     |     |     | 335 |     |
| Gly | Tyr | Gln | Met | Ala | Gln | Pro | Ala | Phe | Ala | Pro | Lys | Asn | Ile | Tyr | Ser |
|     |     |     | 340 |     |     |     |     | 345 |     |     |     |     | 350 |     |     |
| Ile | Met | Gln | Ala | Cys | Trp | Ala | Leu | Glu | Pro | Thr | His | Arg | Pro | Thr | Phe |
|     |     | 355 |     |     |     |     | 360 |     |     |     |     | 365 |     |     |     |
| Gln | Gln | Ile | Cys | Ser | Phe | Leu | Gln | Glu | Gln | Ala | Gln | Glu | Asp | Arg | Arg |
|     | 370 |     |     |     |     | 375 |     |     |     |     | 380 |     |     |     |     |
| Glu | Arg | Asp | Tyr | Thr | Asn | Leu | Pro | Ser | Ser | Ser | Arg | Ser | Gly | Gly | Ser |
| 385 |     |     |     |     | 390 |     |     |     |     | 395 |     |     |     |     | 400 |
| Gly | Ser | Ser | Ser | Ser | Glu | Leu | Glu | Glu | Glu | Ser | Ser | Ser | Glu | His | Leu |
|     |     |     |     | 405 |     |     |     |     | 410 |     |     |     |     | 415 |     |
| Thr | Cys | Cys | Glu | Gln | Gly | Asp | Ile | Ala | Gln | Pro | Leu | Leu | Gln | Pro | Asn |
|     |     |     | 420 |     |     |     |     | 425 |     |     |     |     | 430 |     |     |
| Asn | Tyr | Gln | Phe | Cys |     |     |     |     |     |     |     |     |     |     |     |
|     |     | 435 |     |     |     |     |     |     |     |     |     |     |     |     |     |

( 2 ) INFORMATION FOR SEQ ID NO:11:

( i ) SEQUENCE CHARACTERISTICS:
      ( A ) LENGTH: 566 amino acids
      ( B ) TYPE: amino acid
      ( D ) TOPOLOGY: linear ( i i ) MOLECULE TYPE: peptide ( x ) PUBLICATION INFORMATION:
      ( A ) AUTHORS: Gronwald, R., et al.
      ( C ) JOURNAL: Proc. Natl. Acad. Sci. U.S.A.
      ( D ) VOLUME: 85
      ( F ) PAGES: 3435-3439
      ( G ) DATE: 1988

( x i ) SEQUENCE DESCRIPTION: SEQ ID NO:11:

| Met | Leu | Trp | Gln | Lys | Lys | Pro | Arg | Tyr | Glu | Ile | Arg | Trp | Lys | Val | Ile |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Glu | Ser | Val | Ser | Ser | Asp | Gly | His | Glu | Tyr | Ile | Tyr | Val | Asp | Pro | Val |
|     |     |     | 20  |     |     |     |     | 25  |     |     |     |     | 30  |     |     |
| Gln | Leu | Pro | Tyr | Asp | Ser | Thr | Trp | Glu | Leu | Pro | Arg | Asp | Gln | Leu | Val |
|     |     |     | 35  |     |     |     |     | 40  |     |     |     |     | 45  |     |     |
| Leu | Gly | Arg | Thr | Leu | Gly | Ser | Gly | Ala | Phe | Gly | Gln | Val | Val | Glu | Ala |
|     |     |     | 50  |     |     |     |     | 55  |     |     |     |     | 60  |     |     |

```
Thr  Ala  His  Gly  Leu  Ser  His  Ser  Gln  Ala  Thr  Met  Lys  Val  Ala  Val
65                       70                  75                            80

Lys  Met  Leu  Lys  Ser  Thr  Ala  Arg  Ser  Ser  Glu  Lys  Gln  Ser  Leu  Met
                    85                  90                       95

Ser  Glu  Leu  Lys  Ile  Met  Ser  His  Leu  Gly  Pro  His  Leu  Asn  Val  Val
                    100                 105                      110

Asn  Leu  Leu  Gly  Ala  Cys  Thr  Lys  Gly  Gly  Pro  Ile  Tyr  Ile  Ile  Thr
               115                 120                      125

Glu  Tyr  Cys  Arg  Tyr  Gly  Asp  Leu  Val  Asp  Tyr  Leu  His  Arg  Asn  Lys
     130                 135                      140

His  Thr  Phe  Leu  Gln  Arg  His  Ser  Asn  Lys  His  Cys  Pro  Pro  Ser  Ala
145                      150                 155                           160

Glu  Leu  Tyr  Ser  Asn  Ala  Leu  Pro  Val  Gly  Phe  Ser  Leu  Pro  Ser  His
                    165                 170                      175

Leu  Asn  Leu  Thr  Gly  Glu  Ser  Asp  Gly  Gly  Tyr  Met  Asp  Met  Ser  Lys
               180                 185                      190

Asp  Glu  Ser  Ile  Asp  Tyr  Val  Pro  Met  Leu  Asp  Met  Lys  Gly  Asp  Ile
          195                 200                 205

Lys  Tyr  Ala  Asp  Ile  Glu  Ser  Pro  Ser  Tyr  Met  Ala  Pro  Tyr  Asp  Asn
     210                 215                 220

Tyr  Val  Pro  Ser  Ala  Pro  Glu  Arg  Thr  Tyr  Arg  Ala  Thr  Leu  Ile  Asn
225                      230                 235                           240

Asp  Ser  Pro  Val  Leu  Ser  Tyr  Thr  Asp  Leu  Val  Gly  Phe  Ser  Tyr  Gln
                    245                 250                      255

Val  Ala  Asn  Gly  Met  Asp  Phe  Leu  Ala  Ser  Lys  Asn  Cys  Val  His  Arg
               260                 265                      270

Asp  Leu  Ala  Ala  Arg  Asn  Val  Leu  Ile  Cys  Glu  Gly  Lys  Leu  Val  Lys
          275                 280                 285

Ile  Cys  Asp  Phe  Gly  Phe  Ala  Arg  Asp  Ile  Met  Arg  Asp  Ser  Asn  Tyr
     290                 295                 300

Ile  Ser  Lys  Gly  Ser  Thr  Tyr  Leu  Pro  Leu  Lys  Trp  Met  Ala  Pro  Glu
305                      310                 315                           320

Ser  Ile  Phe  Asn  Ser  Leu  Tyr  Thr  Thr  Leu  Ser  Asp  Val  Trp  Ser  Phe
                    325                 330                      335

Gly  Ile  Leu  Leu  Trp  Glu  Ile  Phe  Thr  Leu  Gly  Gly  Thr  Pro  Tyr  Pro
               340                 345                      350

Glu  Leu  Pro  Met  Asn  Asp  Gln  Phe  Tyr  Asn  Ala  Ile  Lys  Arg  Gly  Tyr
          355                 360                 365

Arg  Met  Ala  Gln  Pro  Ala  His  Ala  Ser  Asp  Glu  Ile  Tyr  Glu  Ile  Met
     370                 375                 380

Gln  Lys  Cys  Trp  Glu  Glu  Lys  Phe  Glu  Thr  Arg  Pro  Pro  Phe  Ser  Gln
385                      390                 395                           400

Leu  Val  Leu  Leu  Leu  Glu  Arg  Leu  Leu  Gly  Glu  Gly  Tyr  Lys  Lys  Lys
                    405                 410                      415

Tyr  Gln  Gln  Val  Asp  Glu  Glu  Phe  Leu  Arg  Ser  Asp  His  Pro  Ala  Ile
               420                 425                      430

Leu  Arg  Ser  Gln  Ala  Arg  Phe  Pro  Gly  Ile  His  Ser  Leu  Arg  Ser  Pro
          435                 440                 445

Leu  Asp  Thr  Ser  Ser  Val  Leu  Tyr  Thr  Ala  Val  Gln  Pro  Asn  Glu  Ser
     450                 455                 460

Asp  Asn  Asp  Tyr  Ile  Ile  Pro  Leu  Pro  Asp  Pro  Lys  Pro  Asp  Val  Ala
465                      470                 475                           480

Asp  Glu  Gly  Leu  Pro  Glu  Gly  Ser  Pro  Ser  Leu  Ala  Ser  Ser  Thr  Leu
```

-continued

|  |  |  | 485 |  |  |  |  |  | 490 |  |  |  | 495 |  |  |
|---|---|---|---|---|---|---|---|---|---|---|---|---|---|---|---|
| Asn | Glu | Val | Asn<br>500 | Thr | Ser | Ser | Thr | Ile<br>505 | Ser | Cys | Asp | Ser | Pro<br>510 | Leu | Glu |
| Leu | Gln | Glu<br>515 | Glu | Pro | Gln | Gln | Ala<br>520 | Glu | Pro | Glu | Ala | Gln<br>525 | Leu | Glu | Gln |
| Pro | Gln<br>530 | Asp | Ser | Gly | Cys | Pro<br>535 | Gly | Pro | Leu | Ala | Glu<br>540 | Ala | Glu | Asp | Ser |
| Phe<br>545 | Leu | Glu | Gln | Pro | Gln<br>550 | Asp | Ser | Gly | Cys | Pro<br>555 | Gly | Pro | Leu | Ala | Glu<br>560 |
| Ala | Glu | Asp | Ser | Phe<br>565 | Leu |  |  |  |  |  |  |  |  |  |  |

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TCGACGCGCG ATGGAG                                                    1 6
```

RECOMBINANT KINASE INSERT DOMAIN CONTAINING RECEPTOR AND GENE ENCODING SAME

FIELD OF THE INVENTION

This application is the U.S. National Stage of PCT/US92/01300, filed Feb. 20, 1992 filed under 35 USC § 371.

This invention relates to the DNA sequence encoding a novel human growth factor receptor which is a type III receptor tyrosine kinase. The receptor is referred to as Kinase insert Domain containing Receptor (KDR) and binds specifically to the growth factor vascular endothelial cell growth factor (VEGF). This invention also relates to the amino acid sequence of the receptor.

BACKGROUND OF THE INVENTION

Growth factors are small molecules which regulate normal cell growth and development through interaction with cell surface receptors. The receptors for a number of growth factors are referred to as tyrosine kinases; that is, binding of growth factor to the receptor stimulates an increased phosphorylation of tyrosine amino acids within the receptor; this is turn leads to cellular activation (Bibliography 1).

There is increasing evidence that genetic alterations affecting the expression of receptor tyrosine kinases (RTK) can contribute to the altered cell growth associated with cancer. This conclusion is supported by the frequent identification of RTK as products of the oncogenes for many of the acutely transforming retroviruses (e.g., 2,3,4) and the overexpression of RTK in certain cancers (5). The identification of a novel RTK may lead to a better understanding of cell growth under both normal and transforming circumstances.

The amino acid sequence in the catalytic domain of all tyrosine kinases has been conserved (6). Detailed analysis of the amino acid sequences within the catalytic and noncatalytic domains of RTK indicates the existence of distinct structural subtypes. One group of RTK (designated type III) includes the ckit proto-oncogene and the receptors for platelet derived growth factor (PDGF) and colony stimulating factor-1 (CSF-1).

The most unusual feature of this subtype is that its catalytic (kinase) domain is interrupted by a long insertion sequence of 12–102 amino acids (the kinase insert domain) The two peptides constituting the kinase domain are conserved between the receptors, while the sequence of the kinase insert domain is unique for each receptor.

Several approaches have been tried in order to identify novel RTK, including low-stringency screening of cDNA libraries with previously characterized DNA probes (7). More recently, a technique has been developed that is capable of greatly facilitating the identification of novel genes for which some sequence data are known. The polymerase chain reaction (PCR) has been used to identify novel members of several gene families including those of guanine nucleotide regulatory proteins (8) and protein phosphatases (9). PCR has been used to identify novel tyrosine kinase genes (10), though the primers used in that study were designed from DNA segments contained in all tyrosine kinases, rather than being specifically directed against RTK. It is a continuing goal to identify receptors for growth factors.

The elucidation of the growth factors, as well as their receptors, involved in regulating endothelial cell function is critical for the understanding of how new blood vessels are formed (angiogenesis). Angiogenesis plays a significant role in both normal and pathological events such as embryogenesis, progression of ocular diseases, and wound healing (11). In particular, angiogenesis is an important process for the growth of tumors (11). Angiogenesis is a complex process involving endothelial cell proliferation, migration, and tissue infiltration. These events are stimulated by growth factors which either (i) act directly on endothelial cells (12,13), or (ii) act indirectly by inducing host cells to release specific endothelial cell growth factors (11). One member of the first group is vascular endothelial cell growth factor (VEGF), also known as vascular permeability factor (14–16). Besides its angiogenic activity, VEGF displays the physiological function of increasing the permeability of capillary vessels to different macromolecules (14).

SUMMARY OF THE INVENTION

The present invention relates to novel DNA segments which together comprise a gene which encodes type III RTK. The type III RTK encoded by the gene is designated the KDR protein (which stands for Kinase insert Domain containing Receptor). The KDR protein binds specifically to the growth factor VEGF (vascular endothelial cell growth factor).

The DNA segments are identified and isolated through the use of PCR technology. The overall strategy is summarized as follows:

PCR is used to amplify the DNA segments corresponding to the kinase insert domains of type III receptor tyrosine kinase genes in an endothelial cell library designated HL10246 (Clontech Laboratories, Inc., Palo Alto, Calif.). Degenerate oligonucleotide primers are designed which are complementary to conserved tyrosine kinase domains flanking the kinase insert domains of known type III receptor tyrosine kinases. These primers are used in the PCR procedure. DNA probes, designed from the DNA sequence of the PCR product, are then used to identify cDNA clones of the receptor gene from the original cDNA library.

In particular, the present invention relates to specific oligonucleotides which, when used as primers for PCR, allow for the amplification of DNA segments corresponding to the kinase insert domains of type III RTK genes.

In a principal embodiment, the present invention is directed to three overlapping DNA segments (designated BTIII081.8, BTIII129.5 and BTIV169) which comprise the entire coding region of this novel gene, namely, 4,068 nucleotides extending to the 3' end.

These DNA segments are isolated from a human endothelial cell cDNA library and together comprise the gene coding for a novel type III receptor tyrosine kinase. The human gene containing these DNA segments is referred to hereinafter as KDR (which stands for Kinase insert Domain containing Receptor) or, alternatively, as kdp (which stands for Kinase insert Domain containing Protein). The use of the term KDR is intended to include any DNA segments which form the human gene which encodes the novel type III RTK of this application.

The DNA segments embodied in this invention are isolated from human sources. The present invention comprises DNA segments, and methods for using these DNA segments, which allow for the identification of a closely related gene in mouse DNA. The methods developed in this invention can be readily used by those skilled in the art for the identification and isolation of closely-related homologues in other species. Therefore, the present invention also embodies all DNA segments from species other than human which encode proteins having substantially the same amino acid sequence as that encoded by the kdp gene.

The present invention further relates to methods developed for the detection of mRNA's produced as a result of transcription of the sense strands of the DNA segments of this invention. Messenger RNA prepared from bovine endothelial cells are used in developing these methods. The ability to detect mRNA for a novel RTK may ultimately have medical benefit, especially in light of recent observations that the mRNA for certain RTKs are overexpressed in some cancers (5).

The methods developed in the present invention for detecting MRNA expressed by the kdp gene can be readily used by those of ordinary skill in the art for the detection of mRNA species related to the kdp gene in any cell type and from any species. For this reason, the present invention embodies all mRNA segments which are the result of transcription of the kdp gene.

The present invention relates to methods for expression of the receptor protein, for example, in CMT-3 cells of monkey kidney origin. The receptor protein, portions thereof, and mutated forms of the receptor protein may be expressed in many other cells by those skilled in the art using methods similar to those described in this application. For this reason, the present invention embodies all proteins encoded by the human KDR gene and proteins encoded by related genes found in other species.

The present invention further relates to methods for studying the interaction of VEGF to the expressed KDR protein. Recent work in the literature (17) indicates that VEGF is one member of a family of related proteins, and the interaction of growth factors similar to VEGF with the KDR protein can readily be studied by those skilled in the art using methods similar to those described in this application. These methods can readily be modified to study the interaction of candidate pharmaceuticals with the KDR protein towards the goal of developing an antagonist or agonist of VEGF action. For this reason, the present invention embodies methods for studying the interaction of VEGF and VEGF-related growth factors with the KDR protein.

BRIEF DESCRIPTION OF THE DRAWINGS

FIG. 2 depicts the two sets of primers used for PCR (SEQ ID NO: 1 and 2). The nucleotide sequences in appropriate regions of the four known type III receptor tyrosine kinase cDNAs are aligned and degenerate oligonucleotide primers are designed based upon the consensus sequences.

FIGS. 4A and 4B depict the DNA sequence of the two PCR products (Panel A: 363 bp segment derived from the 420 bp product (SEQ ID NO: 3); Panel B: 251 bp product (SEQ ID NO: 4)). The two products are purified by agarose gel electrophoresis, digested with SalI and EcoRI, and cloned into the plasmid vector pBlueScribe(+)™ (Strategene; San Diego, Calif.). The 420 bp PCR product is digested to 363 bp during this procedure. The DNA sequences for the primers used in the amplification are underlined.

FIG. 7 depicts the DNA and predicted amino acid sequence of KDR, plus the stop codon (nucleotides 1-4071 of SEQ ID NO:7 and amino acids 1-1356 of SEQ ID NO:8. The sequence of the DNA segment amplified by PCR is underlined (nucleotides 2749–3105 of SEQ ID NO. 7). Cysteine residues in the putative extracellular domain are circled. Potential N-linked glycosylation sites are indicated by an asterisk. The putative membrane spanning region is enclosed in a box (nucleotides 2293–2367 of SEQ ID NO. 7).

FIG. 9 depicts a comparison of the predicted amino acid sequence in the putative intracellular portion of the KDR protein to the ckit proto-oncogene (SEQ ID No: 9) (3), the CSF-1 receptor (SEQ ID NO: 10) (4), and the PDGF receptor (SEQ ID NO: 11) (18). Exact matches are indicated by an asterisk. Gaps are introduced to achieve maximum alignment. The putative ATP recognition site is indicated by three asterisks.

DETAILED DESCRIPTION OF THE INVENTION

Figure 1:
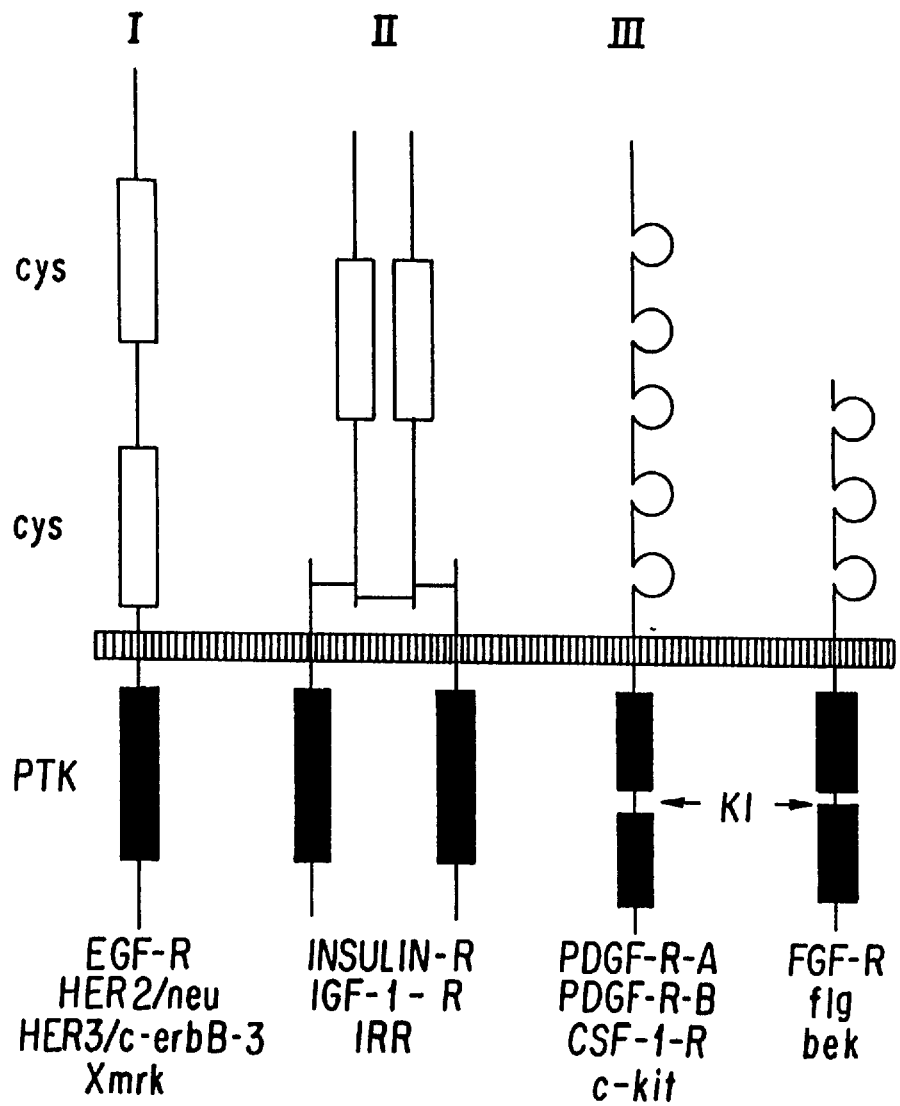
FIG. 1 depicts a schematic representation of three receptor tyrosine kinase subclasses (6). KI is kinase insert domain; PTK is kinase domain; cys is cysteine rich region.

The strategy used to discover the DNA segments for the novel type III RTK gene begins with the design of two degenerate oligonucleotide primers based upon their homology to specific regions of the kinase domains of known RTK genes (FIG. 2) (3,4,7,18). In one embodiment, the polymerase chain reaction is then used to amplify DNA segments from a human endothelial cell cDNA library (designated HL 10246). The CDNA products from this step are each cloned into a plasmid vector designated pBlueScribe+™ (Strategene, San Diego, Calif.) and sequenced. Oligonucleotide probes are designed from potentially interesting sequences in order to screen the cDNA library for more full length clones of the novel cDNA.

The strategy just described provides several novel elements: 1) the DNA sequences of the oligonucleotide primers used during PCR; 2) the DNA sequence of the products generated by the polymerase chain reaction; and 3) the DNA sequence of the final cloned DNA segments. Each of these elements of the invention described in this application will now be discussed in detail.

FIG. 2 shows the rationale for choosing the oligonucleotide primers used in the PCR. The primers are designed to allow for the PCR amplification of the kinase insert domain of type III RTK genes. In order to design the primers, the DNA sequences of known type III RTK genes are aligned in specific regions of their catalytic domains, and a consensus sequence is chosen. The regions of the catalytic domains chosen in designing the primers flank the kinase insert domains of the receptor genes.

Primer 1 (SEQ ID No: 1) is designed from a region of the kinase domain 5' to the kinase insert domain, and consists of a mixture of four different 21mers. Primer 2 (SEQ ID NO: 2) is designed from a region of the kinase domain 3' to the kinase insert domain, and consists of a mixture of sixteen different 29mers with one inosine, indicated in SEQ ID NO: 2 by "N".

SalI and EcoRI restriction sites are included at the 5' end of primers 1 and 2, respectively, to facilitate the subcloning of the amplified PCR products into plasmid vectors. Those skilled in the art may use other restriction sites; other minor modifications in the protocol above permits the design of primers without the inclusion of restriction sites.

The selection of these specific primers constitutes a novel approach towards identifying novel type III RTK genes. It had previously been shown (10) that primers designed from DNA sequences common to all tyrosine kinases allows for the identification of novel proteins. The present invention is the first to contemplate the use of PCR to specifically target type III RTK.

The protocol used for PCR is as follows: Human endothelial cell cDNA (designated HL10246) is denatured by boiling and submitted to 30 cycles of PCR using 1 nmol of both primers in a final volume of 100 μl. The timing is 1.5 minutes at 92° C., 2 minutes at 50° C., and 2 minutes at 74° C. DNA from 5 μl of sample is separated on a 1% agarose gel and stained with ethidium bromide.

Figure 3:
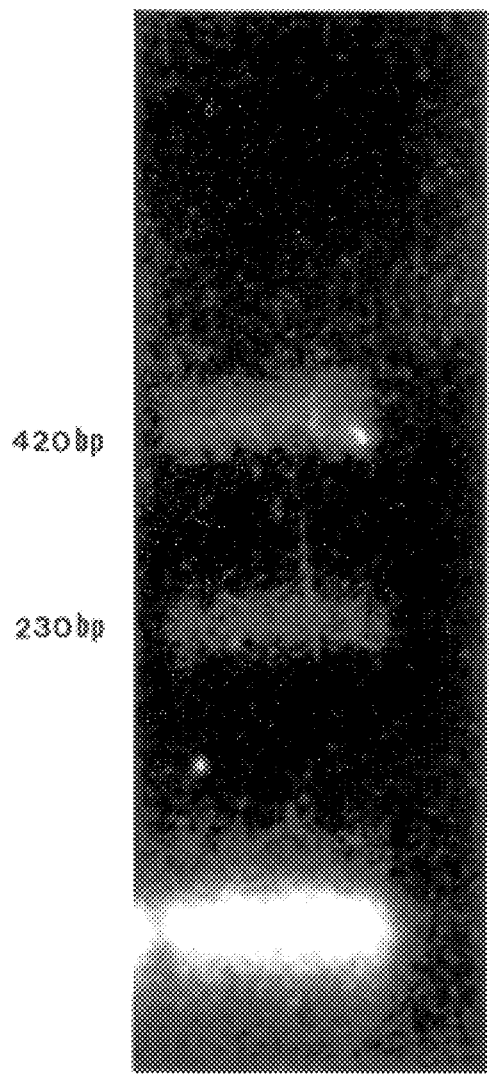
FIG. 3 depicts the amplification of the kinase insert domains using PCR. DNA segments encoding the kinase insert domains of type III receptor tyrosine kinases are amplified by PCR. A sample (5 $\mu$l) is run on a 1.0% agarose gel which is stained with ethidium bromide. DNA size standards (123 bp ladder; Bethesda Research Laboratories, Bethesda, Md.) are run as well.

FIG. 3 shows the results of the PCR amplification. Two DNA products, with sizes 251 bp (SEQ ID NO: 4) and 420 bp, are visible when a sample of the reaction is electrophoresed on a 1.0% agarose gel and stained with ethidium bromide. The sizes of the two products are within the range expected for type III RTK genes (products derived from the FGF and PDGF receptor genes, which have the smallest and largest known kinase insert domains, would be 230 and 510 bp, respectively (20, 21).

Figures 4A, 4B:
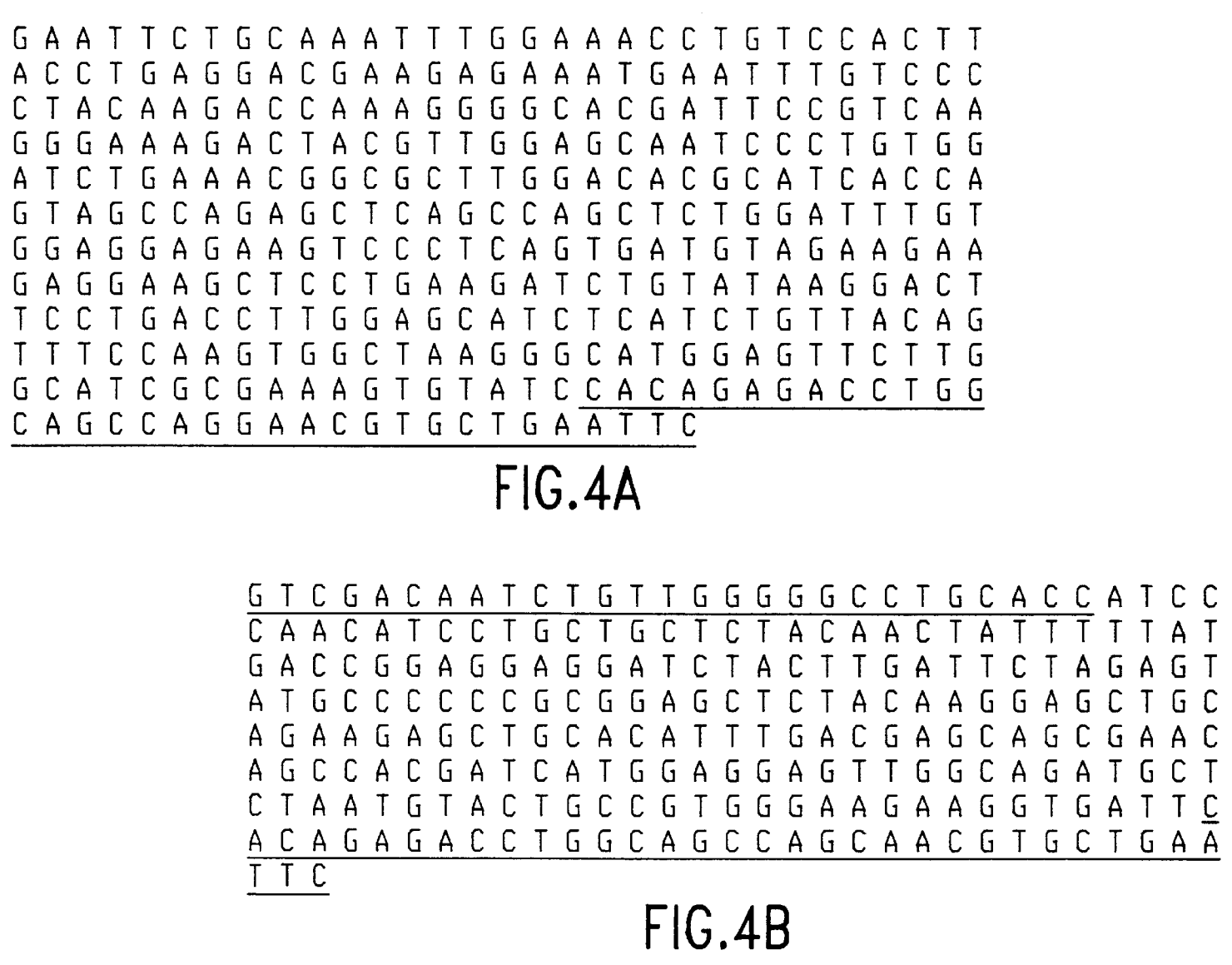

The DNA from four contiguous lanes with sizes ranging from 200 to 600 bp is electrophoresed onto DEAE filter paper, eluted from the paper with salt, and ethanol precipitated. The samples are incubated with 5 units of EcoRI and SalI. The restriction enzymes digest the 420 bp DNA segment to a 363 bp DNA segment (SEQ ID NO: 3), due to the presence of an EcoRI site within the 420 bp DNA segment (nucleotide 2749, SEQ ID NO: 7). The restriction enzyme digested PCR products are then subcloned into the plasmid vector pBlueScribe(+)™. The recombinant clones are analyzed by sequencing using the dideoxy-method (22) using a United States Biochemical (Cleveland, Ohio) Sequenase Version 2.0 sequencing kit. FIG. 4 shows the DNA sequences for the 251 bp PCR product and the 363 bp DNA segment derived from the 420 bp PCR product.

Figure 5A:
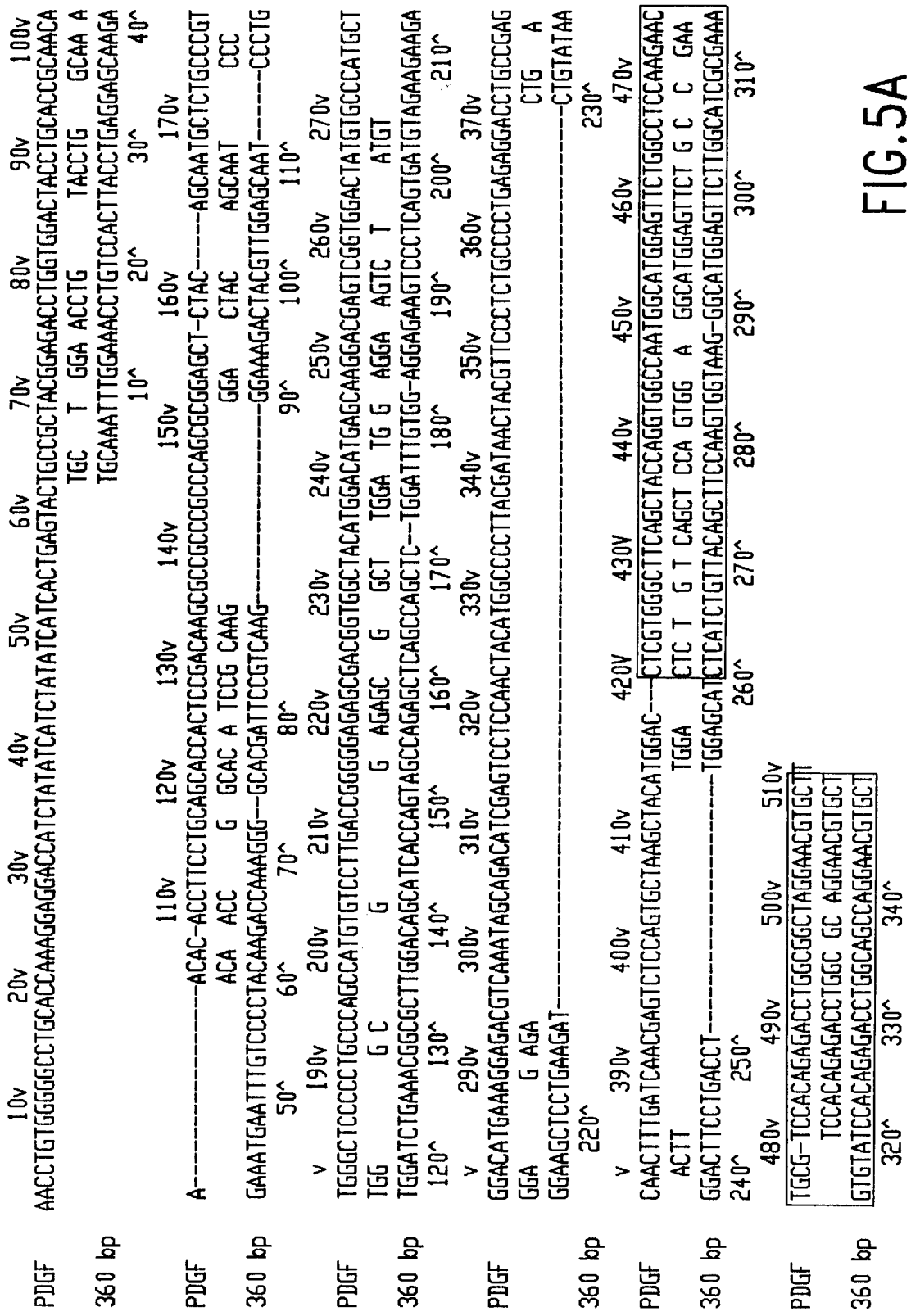
FIG. 5A depicts a computer assisted comparison of the DNA sequence for the 363 bp DNA segment derived from the 420 bp PCR product with the sequence of a DNA segment of the PDGF receptor (SEQ ID NO: 5) (18). A region of strong homology between the 363 bp segment derived from the 420 bp PCR product and the PDGF receptor is contained in a box.

Computer assisted comparison of the DNA sequence for the 363 bp segment of the 420 bp PCR product to databases of known DNA sequences reveals that the sequence is novel, because it shares strong sequence identity with the flanking catalytic domain of known type III RTK genes, but not their kinase insert domains. FIG. 5A compares the DNA sequence for the 363 DNA segment with that for the PDGF receptor gene (SEQ ID No: 5). Similar results are obtained using other type III RTK genes.

Figure 5B:
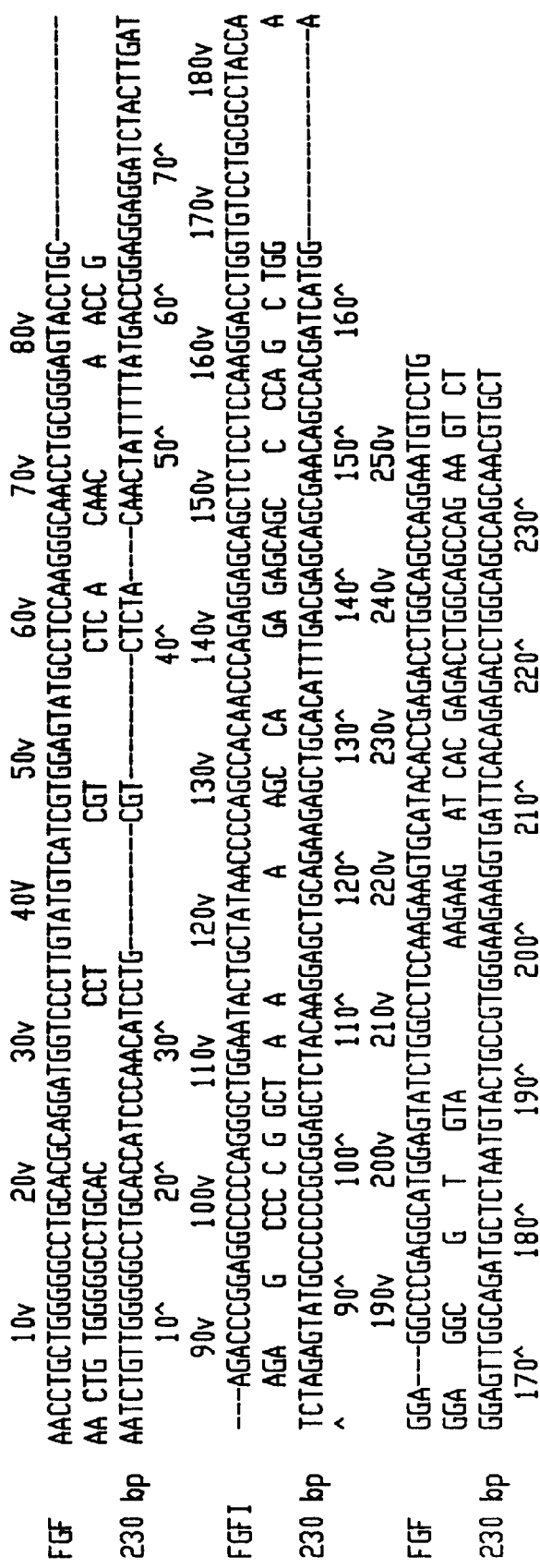
FIG. 5B depicts a computer assisted comparison of the DNA sequence for the 251 bp PCR product with the sequence of a DNA segment of the FGF receptor (SEQ ID NO: 6) (7).

DNA sequencing of the 251 bp PCR product reveals a novel sequence containing both primers used for the amplification, but the sequence shows little homology to known tyrosine kinases. This is depicted in FIG. 5B, which compares the DNA sequence for the 251 bp DNA segment with that for the FGF receptor (SEQ ID NO: 6). For this reason, further analysis of Product 1 is not pursued.

The protocols used during the PCR do not allow for amplification of the kinase insert domains of known receptor tyrosine kinases in the endothelial cell library used because of the low copy number of the message present in the library. There have been many studies on the effect of FGF on endothelial cell function (23,24) although there is evidence that the expression of the FGF receptor is developmentally regulated (7) and it is likely that the library used contains little or no cDNA for the FGF receptor.

An oligonucleotide probe, designed from the DNA sequence of the 363 bp segment, is synthesized (using an ABI 380 DNA Synthesizer) in order to screen the human endothelial cell cDNA library (HL10246) for the isolation of more full length clones containing the 363 bp DNA segment. The probe sequence is chosen from the region of the 363 bp DNA segment which shares little sequence homology with known RTK.

The screening of the endothelial cell cDNA library is conducted as follows: Lambda gtll phage, $10^6$, are adsorbed to E. coli LE392 for 15 minutes at 37° C. prior to plating onto agar plates at a density of $5 \times 10^5$ phage per plate. After allowing the phage plaques to develop at 37° C., plaque lifts are made using nitrocellulose filters, denatured in 0.4N NaCl for 1 minute, and neutralized in 0.5M Tris.HCl, pH 7.3, plus 1.5M NaCl. The filters are washed with 2× standard saline citrate (SSC) and then baked for 1.5 hour in a vacuum oven at 80° C. The filters are probed with an [$^{32}$P] ATP end labeled synthetic oligonucleotide, 5'-TTTCCCTTGACGGAATCGTGCCCCTTTGGT-3', which is the reverse complement of a DNA sequence contained in the PCR amplified product (FIG. 3). Hybridization is performed at 50° C. in 5× SSPE (167 mM NaCl, 10 mM sodium phosphate, pH 7.4, 1 mM EDTA), 2.5× Denhardts, 0.5% sodium dodecyl sulfate (SDS), 100 μg/ml salmon sperm DNA. The filters are washed twice, 20 minutes per wash, with 2× SSC plus 0.1% SDS at room temperature, followed by washing twice at 50° C. with 0.1× SSC plus 0.1% SDS; 20 minutes per wash. Positive clones are identified, picked and plaque purified.

Forty-five positive clones are obtained. Three of these positive clones are plaque purified and their phage DNA isolated. Digestion of the DNA with EcoRI and electrophoresis in agarose indicates that one clone, designated BTIII081.8, contains the largest insert, and subsequent analysis indicates that the DNA insert of this clone overlaps that of the inserts contained in other two purified clones (designated BTIII079.11 and BTIII079.47A).

Figure 6:
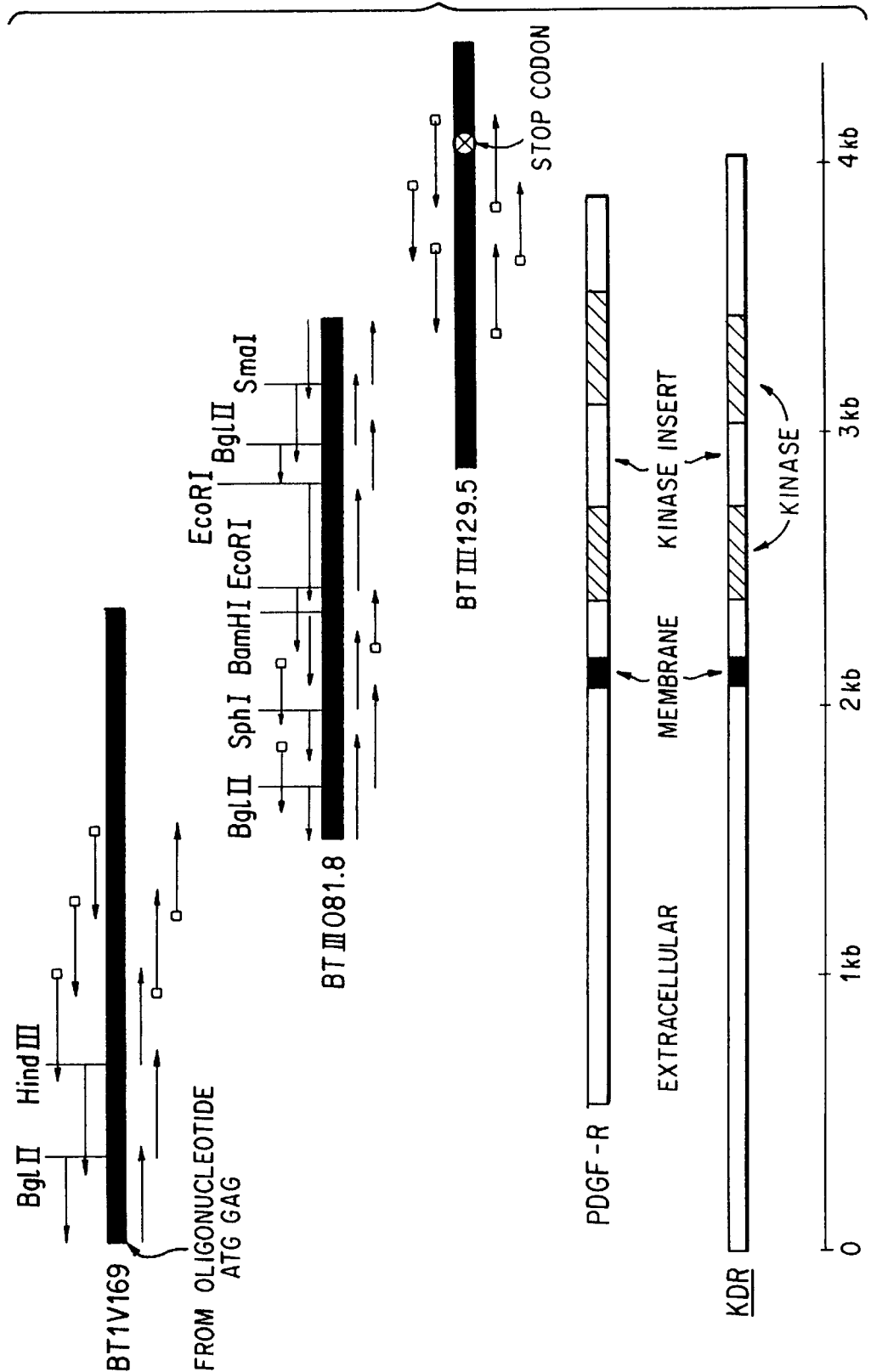
FIG. 6 depicts the strategy used for sequencing the insert portions of clones BTIII081.8 and BTIII129.5 and BTIV169. The sequencing reaction uses either synthetic oligonucleotides (represented by boxes at the start of an arrow), or the M13 universal primer (no box) to initiate the reaction. In some cases, portions of these DNA segments are isolated using the restriction enzymes indicated in the figure, and subcloned back into the plasmid vector pUC118, so that the M13 universal primer can be used. The position of the stop codon in BTIII129.5 is indicated. The coding portions of these DNA segments are shown at the bottom of the figure. The relative positions of the 1) membrane spanning portion, 2) kinase domains, and 3) kinase insert domain are indicated. The position of these structural features within the KDR derived DNA segments is compared in relation to their position in the PDGF-receptor ("PDGF-R").

Digestion of the purified phage DNA of the clone designated BTIII081.8 with EcoRI results in DNA segments of 250 bp, 600 bp, and 1000 bp. Each of these three products is subcloned into the plasmid vector pUC118 and sequenced (FIG. 6 shows the strategy used for sequencing). The orientation of the three fragments is determined by subcloning from the insert a BglII/BglII fragment into pUC118 and sequencing across the EcoRI junctions using a synthetic oligonucleotide to prime the sequencing reaction.

A restriction map is determined for each fragment (FIG. 6). Various restriction site pieces are removed from the plasmids and recloned into pUC118 so that sequencing the resulting plasmids with the universal primer allows for sequencing most of the entire original fragments in both directions. Three oligonucleotide primers are required to sequence the entire cDNA in both directions. For the purposes of this application, this insert contains nucleotides numbered 1510–3406 (SEQ ID NO. 7).

A [$^{32}$ P]CTP-labelled, nick-translated EcoRI-BamHI DNA segment derived from clone BTIII081.8 (nucleotides 1510–2417 of SEQ ID NO. 7) is used as a probe to rescreen the original endothelial cell cDNA library for more 5' full length DNA segments of the gene from which the insert portion of BTIII081.8 is derived. The protocols used to isolate the overlapping clones are identical to that used to isolate BTIII081.8.

A synthetic oligonucleotide probe is designed with 29 nucleotides corresponding to part of the DNA sequence of the insert portion of the clone BTIII081.8 (nucleotides 3297–3325 of SEQ ID NO. 7) in order to rescreen the original endothelial cell cDNA library for more full 3' length DNA segments of the gene from which the insert portion of BTIII081.8 is derived. The protocols used to isolate the overlapping clones are identical to that used to isolate BTIII081.8. Several positive clones for each of the 5' and 3' ends are identified and plaque purified.

One of the clones is designated BTIII200.2. The DNA from BTIII200.2 contains a 3.4 kb insert as determined by EcoRI digestion of the isolated phage DNA. EcoRI digestion of BTIII200.2 results in three DNA fragments. One of these fragments (2.5 kb) is cloned into pUC119 and is designated BTIV006. The clone BTIV006 contains nucleotides numbered 7–2482. As described below, BTIV006 plus nucleotides 1–6 is designated BTIV169. DNA sequencing of the 2.5 kb DNA insert (BTIV169) indicates that it overlaps over one thousand nucleotides of the DNA sequence of the insert portion of the clone BTIII081.8 (FIG. 6) at the 5' end.

A second clone isolated from the cDNA library is designated BTIII129.5. The DNA from BTIII129.5 contains a 2.2 kb insert as determined by EcoRI digestion of the isolated phage DNA. DNA sequencing of the 2.2 kb DNA insert indicates that it overlaps over five hundred nucleotides of the DNA sequence of the insert portion of the clone BTIII081.8 (FIG. 6). The clone BTIII129.5 contains nucleotides numbered 2848–4236 (SEQ ID NO. 7). The DNA sequence for BTIII129.5 contains the stop codon TAA, defining the position of the 3' end of an open reading frame for the novel gene. Except for the first six nucleotides of the gene which are discussed below, these three clones define a gene encoding a growth factor receptor. These three clones define a 4,062 nucleotide sequence of the open reading frame of the gene extending to the 3' end, followed by a 168 nucleotide non-coding region (SEQ ID NO. 7). A sample of a lambda gtll phage harboring the clone BTIII081.8 has been deposited with the American Type Culture Collection, 12301 Parklawn Drive, Rockville, Md. 20852, U.S.A., and has been assigned ATCC accession number 40,931. A sample of a lambda gtll phage harboring the clone BTIII129.5 has been deposited with the American Type Culture Collection and has been assigned ATCC accession number 40,975. For reasons discussed below, a sample of the clone BTIV006 was not deposited.

The aforementioned DNA segments (BTIII081.8, BTIII129.5, and BTIII200.2 (or BTIV006) encode 4062 nucleotides of the coding portion of a novel gene. The cDNA clones are incomplete in that a transcription initiation coding for methionine is missing. After the isolation of these clones, Matthews et al. (25) reported the cloning of a gene homologue of KDR in mouse, which was referred to as Flk-1. Analysis of the nucleic acid and amino acid sequence of Flk-1 indicated that the addition of six nucleotides to the 5' end of the isolated KDR clones would provide for a complete coding region.

To achieve this, an EcoRI-BamHI restriction fragment of BTIV200.2 is cloned into the plasmid pBlueScript KS™ (Strategene, La Jolla, Calif.). The 5' end of the inserted DNA is blunt ended with Klenow polymerase and Mung Bean nuclease. Next, the synthetic oligonucleotide TCGACGCGCG ATG GAG (SEQ ID NO. 12) is cloned into this vector. The oligonucleotide contains the sequence ATG GAG in frame with the downstream DNA insert. These nucleotides (ATG GAG) encode the amino acids methionine and glutamic acid, the first two amino acids encoded by the KDR gene. The resulting plasmid vector is designated BTIV140. This plasmid is purified on a CsCl gradient.

The purified plasmid is designated BTIV169. The insert of BTIV169 contains nucleotides 1–2400 (SEQ ID NO. 7) of the KDR gene. A sample of the plasmid pBlueScript KS™ which contains the clone BTIV169 has been deposited with the American Type Culture Collection and has been assigned ATCC accession number 75200.

Thus, together the clones BTIII081.8, BTIII129.5 and BTIV169 comprise the entire open reading frame of 4,068 nucleotides for the novel KDR gene. As will be discussed below, the KDR gene expresses the novel KDR receptor which binds specifically to the growth factor VEGF.

Figure 8:
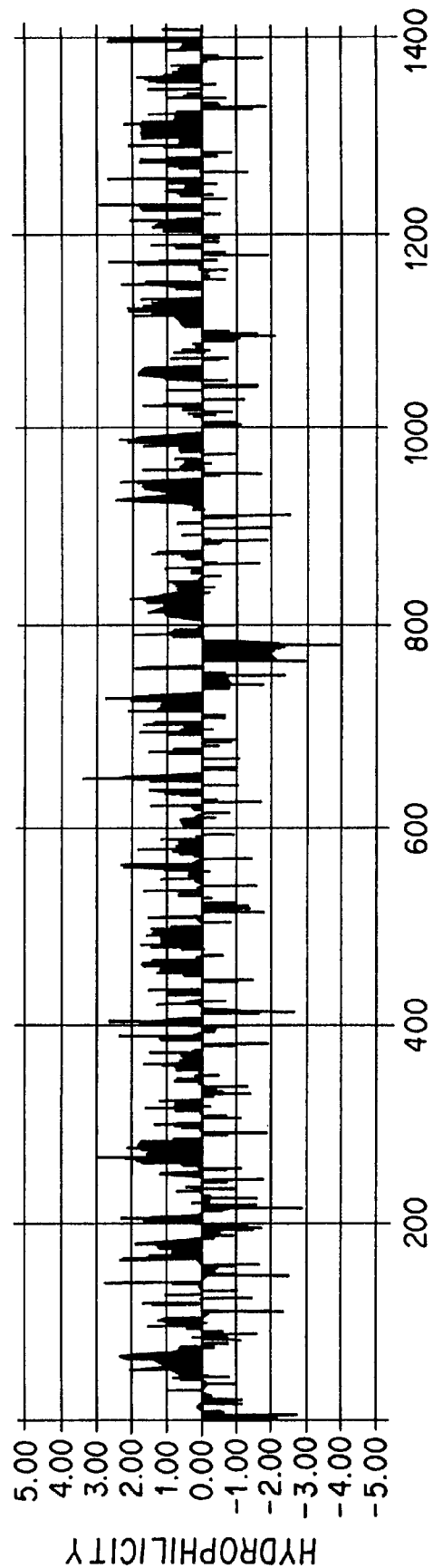
FIG. 8 depicts a hydropathy plot of the predicted amino acid sequence for the KDR protein.

DNA sequencing of BTIII081.8, BTIII129.5 and BTIV169 (SEQ ID NO. 7) shows that the newly isolated gene is similar to, but distinct from, previously identified type III RTK. The predicted amino acid sequence (SEQ ID NO. 7) contains several structural features which demonstrate that the novel gene is a type III RTK. These structural features are summarized as follows:

1) A hydropathy plot of the predicted amino acid sequence indicates a single membrane spanning region (see FIG. 8). This is characteristic of a type III RTK (FIG. 7).
2) The putative amino-terminal 762 amino acid portion of the receptor has structural features of extracellular receptor ligand binding domains (1), including regularly spaced cysteines and 18 potential N-linked glycosylation sites (FIG. 7).
3) The predicted amino acid sequence of the carboxy-terminal 530 amino acid portion contains an ATP-binding site at lysine 868, 22 amino acids downstream from the consensus ATP recognition sequence Gly-X-Gly-X-X-Gly (26) (FIG. 8).
4) Within the kinase domain there is a 55–60% identical match in amino acid sequence to three other type III receptor tyrosine kinases: ckit proto-oncogene (SEQ ID NO: 9), CSF-1 (SEQ ID NO: 10) and PDGF (SEQ ID NO: 11) (FIG. 9).
5) The predicted kinase domain contains a kinase insert domain of approximately 71 amino acids. As indicated in FIG. 9, this portion of the amino acid sequence shares little sequence homology with other type III RTK.

The endothelial cell library can be further screened to isolate the 5' untranslated region and genomic clones can be generated so as to isolate the promoter region for the KDR gene.

In addition to the DNA sequence described for the KDR gene (SEQ ID NO. 7), the present invention further comprises DNA sequences which, by virtue of the redundancy of the genetic code, are biologically equivalent to the sequences which encode for the receptor, that is, these other DNA sequences are characterized by nucleotide sequences which differ from those set forth herein, but which encode a receptor having the same amino acid sequences as those encoded by the DNA sequences set forth herein.

In particular, the invention contemplates those DNA sequences which are sufficiently duplicative of the sequence of SEQ ID NO. 7 so as to permit hybridization therewith under standard high stringency Southern hybridization conditions, such as those described in Sambrook et al. (27), as well as the biologically active proteins produced thereby.

This invention also comprises DNA sequences which encode amino acid sequences which differ from those of the novel receptor, but which are the biological equivalent to those described for the receptor. Such amino acid sequences may be said to be biologically equivalent to those of the receptor if their sequences differ only by minor deletions from or conservative substitutions to the receptor sequence, such that the tertiary configurations of the sequences are essentially unchanged from those of the receptor.

For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Nucleotide changes which result in alteration of the N-terminal or C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. Each of the proposed modifications is well within the routine skill in the art, as is determination of retention of biological activity of the encoded products. Therefore, where the terms "KDR gene" or "KDR protein" are used in either the specification or the claims, each will be understood to encompass all such modifications and variations which result in the production of a biologically equivalent protein.

In addition to the full length gene and protein, the invention encompasses biologically active fragments of each. By "biologically active" is meant a protein fragment which qualitatively retains the receptor activity of the larger KDR protein, or, in the case of a nucleotide sequence, which encodes such a protein fragment. It also refers, for purposes of antibody production, to fragments which are capable of eliciting production of antibodies capable of binding to the receptor protein.

Figure 10:
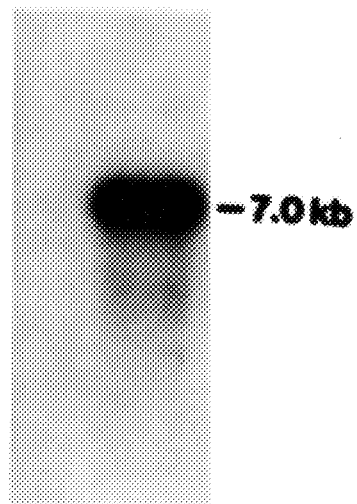
FIG. 10 depicts the identification of kdp receptor mRNA by Northern blot analysis. Five micrograms of bovine aortic endothelial cell polyA+ RNA are used. A nick-translated [$^{32}$P] CTP-labelled EcoRI/BamHI DNA segment (nucleotides 1510–2417 of SEQ ID NO. 7) is used as a probe. Autoradiography is for 36 hours.

To determine the size of the mRNA transcribed from the kdp gene, Northern blot hybridization experiments are carried out using an EcoRI/BamHI DNA segment (nucleotides 1510–2417, SEQ ID NO. 7) as a hybridization probe. The DNA used for the probe does not contain any portion of the putative kinase domain, and shares little sequence homology to other tyrosine kinases. The Northern blot analysis (FIG. 10) shows that a 7 kb band is visualized in cytoplasmic poly(A)+ RNA of ABAE bovine aortic endothelial cells. This transcript differs in size from previously reported transcripts for known type III RTK (7,18).

The isolated cDNA is significant for several reasons. The cDNA encodes a novel type III receptor tyrosine kinase. The homology between the sequence of this cDNA and that of other receptors, as well as structural properties implied by the predicted amino acid sequence confirm the relationship. Receptors for growth factors should have tremendous utility in drug development as they face the outside of the cell and thus are among the best targets for drugs. In addition, the cellular levels of some receptors, in particular the neu proto-oncogene, increase during some cancers. This has been taken advantage of in designing diagnostic tests for these cancers.

Figure 11:
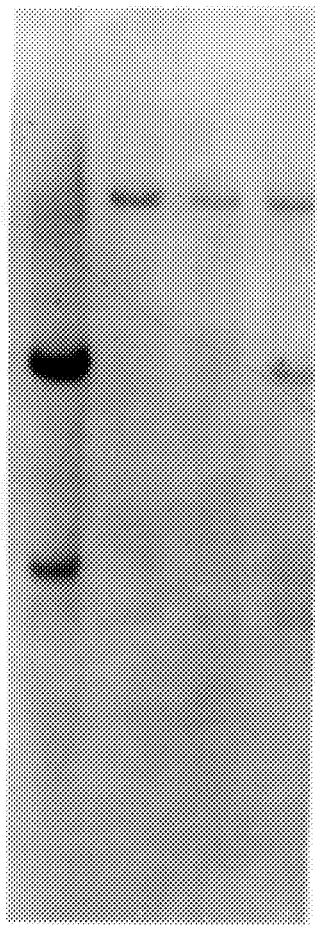
FIG. 11 depicts the kdp gene in human and mouse DNA by Southern blot analysis. A nick translated [$^{32}$P]CTP-labelled EcoRI/BamHI DNA segment (nucleotides 1510–2417 of SEQ ID NO. 7) is used as the probe. The probe is hybridized to Southern blots containing EcoRI digested DNA from human (lane 1), mouse (lane 2), and human-mouse hybrid cells (19) (lanes 3 and 4). The DNA used in lane 3 lacks the kdp locus, while DNA used in lane 4 contains the kdp locus.

Southern analysis demonstrates that the kdp gene is present in mouse as well as human DNA. Mouse and human (Hela cell) DNA, 15 $\mu$g of each, are digested with 10 units of EcoRI and electrophoresed on a 0.7% agarose gel. The DNA is transferred onto nitrocellulose. The filter is hybridized to a [$^{32}$P]CTP-labelled CDNA probe made by nick translating an EcoRI/BamHI fragment from the 5' end of the kdp cDNA (nucleotides 1510–2417, SEQ ID NO. 7). Hybridization is conducted at 30° C. in 5× SSPE, 50% formamide, 0.1% SDS, plus 150 µg/ml salmon sperm DNA. The DNA probe hybridizes to Southern blots containing EcoRI digested DNA. After 48 hours, the filter is washed at room temperature in 2× SSC plus 0.1% SDS for 20 minutes, followed by two 20 minute washes at 40° C. with 0.1× SSC plus 0.1% SDS. Autoradiography is then performed for 48 hours. As shown in FIG. 11, radioactively labelled DNA is present in both human and mouse samples. This indicates that the kdp gene is present in both species.

An experiment is conducted to ascertain the genetic locus of kdp on human chromosomes. Thirty-eight cell hybrids from 18 unrelated human cell lines and four mouse cell lines are examined (19). A DNA probe hybridizes to Southern blots which contain EcoRI digested DNA from the human-mouse hybrids (using the procedure and DNA probe for human and mouse tissue described in relation to FIG. 11). Table I sets forth the results of the segregation of kdp with human chromosomes in EcoRI digested human-mouse somatic cell hybrid DNA:

TABLE I

| Chromosome | Concordant # of Hybrids (+/+) | Concordant # of Hybrids (-/-) | Discordant # of Hybrids (+/-) | Discordant # of Hybrids (-/+) | % Discordancy |
|---|---|---|---|---|---|
| 1 | 4 | 19 | 8 | 4 | 34 |
| 2 | 8 | 18 | 5 | 6 | 30 |
| 3 | 11 | 12 | 3 | 9 | 34 |
| 4 | 14 | 24 | 0 | 0 | 0 |
| 5 | 7 | 14 | 7 | 10 | 45 |
| 6 | 7 | 19 | 7 | 5 | 32 |
| 7 | 11 | 14 | 3 | 8 | 31 |
| 8 | 8 | 11 | 6 | 13 | 50 |
| 9 | 3 | 20 | 10 | 4 | 38 |
| 10 | 12 | 9 | 2 | 14 | 43 |
| 11 | 9 | 13 | 4 | 11 | 41 |
| 12 | 9 | 10 | 5 | 14 | 50 |
| 13 | 7 | 18 | 7 | 6 | 34 |
| 14 | 11 | 8 | 3 | 16 | 50 |
| 15 | 9 | 15 | 5 | 8 | 35 |
| 16 | 7 | 19 | 7 | 5 | 32 |
| 17 | 12 | 7 | 2 | 16 | 49 |
| 18 | 11 | 14 | 3 | 10 | 34 |
| 19 | 7 | 18 | 7 | 6 | 34 |
| 20 | 9 | 10 | 5 | 14 | 50 |
| 21 | 11 | 9 | 3 | 15 | 47 |
| 22 | 3 | 16 | 10 | 7 | 47 |
| X | 8 | 10 | 3 | 8 | 38 |

The scoring is determined by the presence(+) or absence (-) of human bands in the hybrids on Southern blots prepared in a similar to those shown in FIG. 11. The scoring is compared to the presence or absence of human chromosomes in each hybrid. A 0% discordancy indicates a matched segregation of the DNA probe with a chromosome. Three fragments, approximately 6.5 kb, 3.1 kb, and 0.7 kb in size are detected in digests of human DNA (FIG. 11), and in all hybrids which had retained human chromosome 4 (Table I). All other chromosomes are excluded in at least 11 discordant hybrids (Table I). The results of FIG. 11 and Table I demonstrate that the genetic locus of kdp is on human chromosome 4.

It is noteworthy that both the ckit (3) and the type A PDGF (28) receptor genes map to human chromosome 4. The finding that the genetic locus of kdp is on human chromosome 4 provides further evidence that the novel receptor of this invention is a type III receptor tyrosine kinase.

The next step after identifying the entire coding portion of the kdp gene is to express the receptor protein encoded by that gene. The receptor protein is then utilized so as to identify the growth factor which binds specifically to the receptor.

The receptor protein is expressed using established recombinant DNA methods. Suitable host organisms include bacteria, viruses, yeast, insect or mammalian cell lines, as well as other conventional organisms. For example, CMT-3 monkey kidney cells are tranfected with a vector containing the complete coding region of the KDR gene.

The complete coding portion of the KDR gene is assembled by sequentially cloning into pUC119 three DNA fragments derived from BTIII081.8, BTIII129.5, and BTIV169. First, a SmaI-EcoRI fragment of clone BTIII129.5 (nucleotides 3152–4236, SEQ ID NO: 7) is blunt ended with Klenow polymerase and introduced into a SmaI site in pUC119. Next, a BamHI-SmaI fragment of clone BTIII081.8 (nucleotides 2418–3151, SEQ ID NO: 7) is introduced at a BamHI-SmaI site. Finally, a SalI-BamHI fragment of clone BTIV169 (nucleotides 1-2417, SEQ ID NO: 7) is introduced at a SalI-BamHI site. Part of the cloning site of pUC119 is contained in the SalI-BamHI fragment, 5' to the KDR gene. In order to clone the complete coding portion into an expression vector, the assembled DNA (in pUC119) is digested with SalI and Asp118 and recloned into the eukaryotic expression vector pcDNA1tkpASP.

This vector is a modification of the vector pcDNA1 (Invitrogen; San Diego, Calif.). Specifically, the ampicillin resistance gene is cloned from pBR322 into pcDNA1. A small SV40 T splice and the SV40 polyadenylation signal are then removed and are replaced with a Herpes Simplex Virus-1 polyadenylation signal. Finally, a cytomegalovirus intermediate early splice is inserted 5' to the cloning site to yield pcDNA1tkpASP.

Transfection of CMT-3 cells is done using DEAE-dextran. Forty-eight hours after transfection, expression of the novel receptor is monitored using Western blot analysis as follows.

An antibody is used to assay the expressed receptor protein. The predicted amino acid sequence of the receptor is used to generate peptide-derived antibodies to the receptor by conventional techniques. The presence of the novel receptor protein is confirmed by Western blot hybridization.

Specifically, a synthetic peptide with 13 residues is synthesized based on the 12 residues corresponding to amino acids 986–997 of the putative amino acid sequence of the KDR protein (SEQ ID NO: 8), with a cysteine residue linked to the lysine (amino acid 997). The cysteine facilitates coupling of the peptide to a macromolecule which functions as a carrier for the peptide. For example, the peptide is coupled to keyhole limpet haemocyanin (KLH) using m-maleimido-benzoyl-N-hydroxysuccinimide ester. Other conventional carriers may be used such as human and bovine serum albumins, myoglobins, β-galactosidase, penicillinase and bacterial toxoids, as well as synthetic molecules such as multi-poly-DL-alanyl-poly-L-lysine and poly-L-lysine.

Rabbits are immunized with the peptide-KLH conjugate to raise polyclonal antibodies. After different periods of time, serum is collected from the rabbits. The IgG fraction of the serum is then purified using a protein A Sepharose column (Pharmacia LKB, Uppsala, Sweden) to obtain the antibody which is designated anti-KDR.PS23.

A sample of the expressed KDR protein is subjected to SDS-PAGE using a 7% acrylamide gel under standard conditions. The protein band is then transferred onto nitrocellulose paper for Western blot analysis and the anti-KDR.PS23 antibody is added at a dilution of 1:1,000 to allow the antibody to react with the protein present. A second antibody, goat anti-rabbit antibody to rabbit IgG, which binds to anti-KDR.PS23, is then added. The detection of proteins which react with the antibodies is performed by autoradiography of bands using an ECL system (Amersham, Chicago, Ill.). The results are depicted in FIG. 12.

Figure 12:
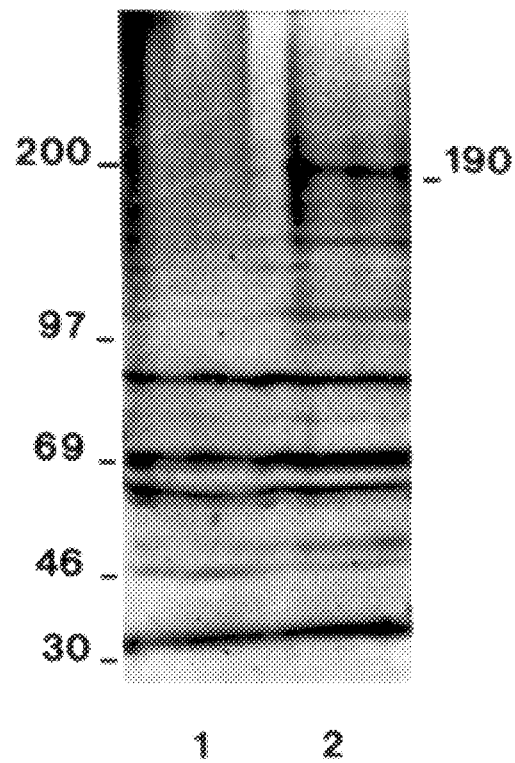
FIG. 12 depicts a Western blot analysis of CMT-3 cells which express the KDR protein. Cells are transfected with either the pcDNA1tkpASP vector alone (lane 1) or with that vector modified to contain the KDR gene (lane 2). 2×10$^5$ cells and 1 microgram of DNA are used for each transfection. Forty-eight hours later, Western blot analysis is performed on the samples using the anti-KDR.PS23 polyclonal antibody at a dilution of 1:1000. Detection of reacting proteins is performed using an ECL system (Amersham, Chicago, Ill.).

FIG. 12 shows that a 190 kD protein is present in the cells transfected with the vector containing the KDR gene, but is absent in cells transfected with vector alone. The size of this protein is consistent with it being encoded by the KDR gene, in that the predicted amino acid sequence for the unglycosylated KDR protein is 156 kD, and that sequence contains 18 putative extracellular glycosylation sites which would account for the balance of the size seen in the 190 kD band.

The expressed receptor is then used to identify the growth factor which interacts with the receptor. In order to test the hypothesis that the KDR protein is a receptor for VEGF, radioligand binding studies are performed. VEGF (provided by D. Gospodarowicz) is radiolabelled with $^{125}$I. Cells are transfected with either the vector pcDNA1tkpASP alone (bars 1 and 2 of FIG. 13) or with the vector containing the KDR gene (bars 3 and 4). Forty-eight hours later, the transfected cell samples are washed with PBS and then incubated for 90 minutes with serum-free media containing 50 pM [$^{125}$I]VEGF (specific activity equal to 4,000 cpm per fmol). Excess nonradioactive VEGF, 5 nM, is added to some samples (bars 2 and 4) to define specific binding sites. The samples are washed with ice cold PBS, and the cells are transferred to gamma-counting tubes using a detergent, 0.1% lubrol.

Figure 13:
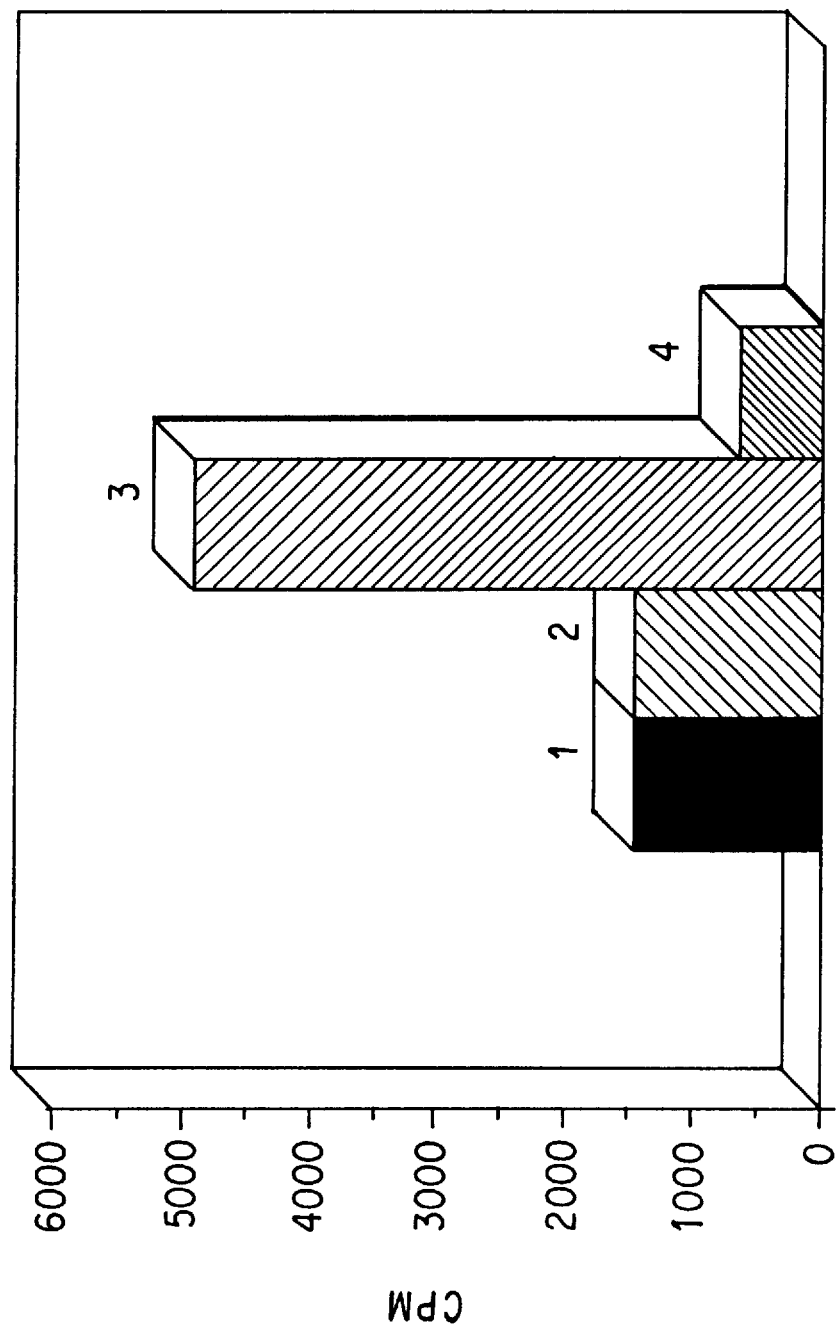
FIG. 13 depicts the results of [$^{125}$I] VEGF binding to CMT-3 cells which express the KDR protein. Cells are transfected with either the vector alone (bars 1 and 2) or with the vector containing the KDR gene (bars 3 and 4). Forty-eight hours later, the samples are washed with phosphate buffered saline (PBS), and incubated with serum-free media containing 50 pM [$^{125}$I] VEGF (specific activity equal to 4,000 cpm per fmol), for 90 minutes. Nonradioactive VEGF, 5 nM, is added to some samples (bars 2 and 4) to define specific binding sites. The samples are washed with ice cold PBS, and the cells are transferred to gamma-counting tubes using 0.1% lubrol.

The results of the radioligand binding studies are depicted in FIG. 13. FIG. 13 shows that CMT-3 cells transfected with vector containing the KDR gene contain specific binding sites for [$^{125}$I]VEGF (compare bars 3 and 4), while cells transfected with vector alone do not (compare bars 1 and 2).

Figure 14:
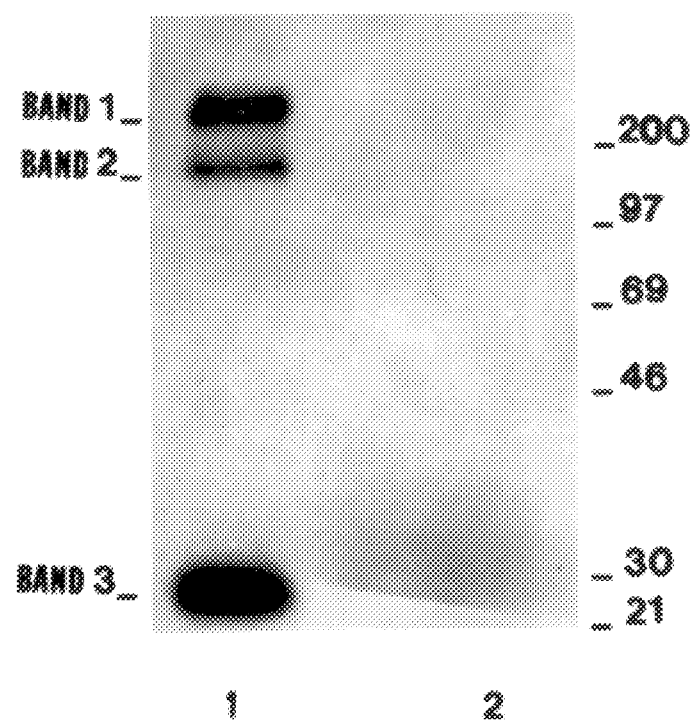
FIG. 14 depicts the results of affinity cross-linking of [$^{125}$I] VEGF to CMT-3 cells which express the KDR protein. CMT-3 cells are transfected with either the vector alone (lane 1) or with the vector containing the KDR gene (lane 2). Forty-eight hours later, the cells are washed in PBS, and serum free media containing 200 pM [$^{125}$I] VEGF is added. After 90 minutes at room temperature, an affinity cross-linker disuccinimidyl suberate, 0.5 mM, is added for 15 minutes. The samples are then prepared for SDS-PAGE autoradiography.

Further evidence that the KDR gene encodes a receptor for VEGF is demonstrated by affinity cross-linking studies (FIG. 14). FIG. 14 depicts the results of affinity cross-linking of [$^{125}$I]VEGF to CMT-3 cells which express the KDR protein. CMT-3 cells are transfected with either the pcDNA1tkpASP vector alone (lane 1 of FIG. 14) or with the vector containing the KDR gene (lane 2). Forty-eight hours later, the cells are washed in PBS, and serum free media containing 200 pM [$^{125}$I]VEGF is added. After 90 minutes at room temperature, an affinity cross-linker disuccinimidyl suberate (Pierce Biochemicals, Rockford, Ill.), 0.5 mM, is added for 15 minutes. The samples are then subjected to SDS-PAGE autoradiography.

Three protein bands are seen in SDS-PAGE autoradiograms from samples of CMT-3 cells transfected with the KDR gene and cross-linked to [$^{125}$I]VEGF (lane 1). The size of band 1 (235 kD) is consistent with it being the 190 kD protein seen by Western blot analysis (FIG. 12), because a 45 kD [$^{125}$I] VEGF dimer plus 190 kD would migrate in a manner identical to band 1. The origin of band 2 is not clear, but may represent an altered glycosylation form of band 1. Band 3 (22.5 kD) is most likely VEGF itself, and can be seen faintly in cells transfected with vector alone (lane 2).

The novel KDR gene of this invention is significant for several reasons. Studies of the cellular mechanisms by which receptors function in signal transduction have led in the past to a better understanding of how cells grow in both normal and diseased states. Receptor tyrosine kinases, in particular, have received a great deal of attention because of the observation that a number of RTK are the cellular counterparts for viral oncogenes, implying a direct correlation between changes in the expression of RTK and cancer. In view of this, it is likely that pharmaceuticals targeted at RTK will inhibit the changes in cell growth associated with cancer. In addition, it is likely that monitoring the levels of expression of RTK will prove valuable in diagnosing the onset of cancer.

The described cDNA is isolated from a human endothelial cell library. Endothelial cells participate in angiogenesis, the formation of new blood capillaries. Previous work directed towards identifying the growth factors which regulate angiogenesis have primarily focused upon FGF (13), although recent evidence has indicated that other growth factors may be involved as well (12,15,29). This evidence consists of the observations that: 1) FGF does not contain a signal sequence (24) and thus may not be secreted from cells in a manner consistent with the tight regulation of angiogenesis, and 2) endothelial cells synthesize FGF and yet are normally resting (15). Our discovery, then, of a novel growth factor receptor may ultimately clarify these inconsistencies and lead to a better understanding of endothelial cell function.

The teachings of this invention can be readily used by those skilled the art for the purpose of testing pharmaceuticals targeted at the KDR protein. Two examples of approaches which can be used for this purpose are now given.

First, the methods described in this invention for studying the interaction of VEGF with KDR protein can be used to test for pharmaceuticals which will antagonize that interaction. For these studies, cells expressing the KDR protein are incubated with [$^{125}$I]VEGF, together with a candidate pharmaceutical. Inhibition of radioligand binding is tested for; significant inhibition indicates the candidate is an antagonist. Permanent expression of the KDR protein in a cell type such as NIH3T3 cells would make these studies less laborious. This can be easily achieved by those skilled in the art using the described methods.

Second, using the teachings of this invention, those skilled in the art can study structural properties of the KDR protein involved in receptor function. This structural information can then be used to more rationally design pharmaceuticals which inhibit that function. Mutagenesis of the KDR gene by well established protocols is one approach, crystallization of the receptor binding site is another.

BIBLIOGRAPHY

1. Yarden Y., and A. Ullrich, Ann. Rev. Biochem., 57, 433–478 (1988).
2. Bargmann, C., et al., Nature, 319, 226–230 (1986).
3. Yarden, Y., et al., EMBO J., 6, 3341–3351 (1987).
4. Coussens, L., et al., Nature, 320, 277–280 (1986).
5. Slamon, D., et al., Science, 244, 707–712 (1989).
6. Ullrich, A. and Schlessinger, J., Cell, 61, 203–212 (1990).
7. Ruta, M., et al., Oncogene, 3, 9–15 (1988).
8. Strathmann, M., et al., Proc. Natl. Acad. Sci., 86, 8698–8702 (1989).
9. Streuli, M., et al., Proc. Natl. Acad. Sci., 86, 8698–8702 (1989).
10. Wilkes, A. F., Proc. Natl. Acad. Sci., 86, 1603–1607 (1989).
11. Folkman, J., and Klagsbrun, M., Science, 235, 442–445 (1987).
12. Ishikawa, F., et al., Nature. 338, 557–562 (1989).
13. Baird, A., and Bohlen, P., in Peptide Growth Factors and Their Receptors, pages 369–418 (Spron, M. B., and Roberts, A. B., eds. 1990).

14. Senger, D. R., et al., *Science*, 219, 983–985 (1983).
15. Gospodarowicz, D., et al., *Proc. Natl. Acad. Sci.*, 86, 7311–7315 (1989).
16. Leung, D. W., et al., *Science*, 246, 1306–1309 (1989).
17. Maglione, D., et al., *Proc. Natl. Acad. Sci.*, 88, 9267–9271 (1991).
18. Gronwald, R., et al., *Proc. Natl. Acad. Sci.*, 85, 3435–3439 (1988).
19. Shows, T., et al., *Somat. Del. Mol. Gen.*, 10, 315–318 (1984).
20. Rainer, G., et al., *Proc. Natl. Acad. Sci.*, 85, 3435–3439 (1988).
21. Lee, P. L., et al., *Science*, 245, 57–60 (1989).
22. Sanger, F., et al., *Proc. Natl. Acad. Sci.*, 74, 5463–5467 (1977).
23. Folkman, J., *Cancer Res.*, 46, 467–473 (1986).
24. Burgess, W. and Maciag, T., *Ann. Rev. Biochem.*, 58, 575–606 (1989).
25. Matthews, W., et al., *Proc. Natl. Acad. Sci.*, 88, 9026–9030 (1991).
26. Hannink, M. and Donoghue, D., *Proc. Natl. Acad. Sci.*, 82, 7894–7898 (1985).
27. Sambrook, J., et al., *Molecule Cloning: A Laboratory Manual*, 2nd ed., Cold Spring Harbor Laboratory Press, Cold Spring Harbor, N.Y. (1989).
28. Matsui, T., et al., *Science*, 243, 800–804 (1989).
29. Conn, G., et al., *Proc. Natl. Acad. Sci.*, 87, 2628–2632 (1990).

---

We claim:

1. A recombinant human DNA sequence encoding a Kinase insert Domain containing Receptor said DNA comprising the nucleotide sequence of SEQ ID NO:7.

2. A lambda gt11 phage harboring the clone BTIII081.8 deposited under ATCC accession number 40,931 or the clone BTIII129.5 deposited under ATCC Accession number 40,975.

3. A plasmid which contains the clone BTIV169 deposited under ATCC accession number 75200.

4. A recombinant human Kinase insert Domain containing Receptor comprising the amino acid sequence of SEQ ID NO:8.

5. A biologically active protein fragment of the recombinant human Kinase insert Domain containing Receptor of claim 4 which binds to vascular endothelial cell growth factor.

6. An oligonucleotide primer consisting of 27 bases and having the sequence of SEQ ID NO: 1.

7. An oligonucleotide primer consisting of 35 bases and having the sequence of SEQ ID NO: 2.

8. A 363 base pair nucleic acid having the sequence of SEQ ID NO: 3.

9. An expression vector comprising the nucleotide sequence of SEQ ID NO:7, wherein the expression vector is capable of expressing a Kinase insert Domain containing Receptor having the amino acid sequence of SEQ ID NO:8 in a transformed host cell.

* * * * *